United States Patent
Hsu et al.

(10) Patent No.: US 12,178,729 B2
(45) Date of Patent: Dec. 31, 2024

(54) HINGE ASSEMBLY FOR AN ORTHOPEDIC DEVICE

(71) Applicant: Ossur Iceland ehf, Reykjavik (IS)

(72) Inventors: Henry Hsu, Foothill Ranch, CA (US); Tim McMorrow, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 231 days.

(21) Appl. No.: 16/831,392

(22) Filed: Mar. 26, 2020

(65) Prior Publication Data

US 2020/0306070 A1    Oct. 1, 2020

Related U.S. Application Data

(60) Provisional application No. 62/823,847, filed on Mar. 26, 2019.

(51) Int. Cl.
*A61F 5/01* (2006.01)

(52) U.S. Cl.
CPC .......... *A61F 5/0102* (2013.01); *A61F 5/0123* (2013.01); *A61F 2005/0139* (2013.01)

(58) Field of Classification Search
CPC ........ A61F 5/01; A61F 5/0102; A61F 5/0123; A61F 5/0125; A61F 5/0127; A61F 5/013; A61F 2005/0132–0181
USPC .................................................... 602/16, 26
See application file for complete search history.

(56) References Cited

U.S. PATENT DOCUMENTS

| | | |
|---|---|---|
| 1,390,915 A | 9/1921 | Loth |
| 2,531,486 A | 11/1950 | Weber |
| 2,883,982 A | 4/1959 | Rainey |
| 3,030,634 A | 4/1962 | Bair |
| 3,099,488 A | 7/1963 | Salvo et al. |
| 3,259,910 A | 7/1966 | Gustave |
| 3,387,305 A | 6/1968 | Shafer |

(Continued)

FOREIGN PATENT DOCUMENTS

| | | |
|---|---|---|
| AU | 2005203062 A1 | 8/2005 |
| DE | 29823435 U1 | 7/1999 |

(Continued)

OTHER PUBLICATIONS

National Cancer Institute—Anatomical Terminology (Year: 2022).*

(Continued)

*Primary Examiner* — Camtu T Nguyen
(74) *Attorney, Agent, or Firm* — Workman Nydegger

(57) ABSTRACT

An orthopedic device has a hinge assembly including: a first hinge arm having a first longitudinal axis, and defining a first end portion having a first opening defining a first axis so the first hinge arm is pivotable about the axis; a second hinge arm having a second longitudinal axis, and defining a second end portion having a second opening defining a second axis and the second hinge arm is pivotable about the second axis. When the first and second longitudinal axes are coaxial, the second opening is arranged along a third longitudinal axis parallel to the first and second longitudinal axes and offset by a distance. The orthopedic device includes additional features including frame components and liner, contoured and formed geometrically with materials providing an improved fit.

8 Claims, 16 Drawing Sheets

(56) References Cited

U.S. PATENT DOCUMENTS

| | | |
|---|---|---|
| 3,669,105 A | 6/1972 | Castiglia |
| 3,779,654 A | 12/1973 | Horne |
| 3,785,372 A | 1/1974 | Craig |
| 3,817,244 A | 6/1974 | Taylor |
| 3,900,898 A | 8/1975 | Ackerman |
| 3,901,223 A | 8/1975 | May |
| 3,902,482 A | 9/1975 | Taylor |
| 3,923,047 A | 12/1975 | Chant |
| 3,928,872 A | 12/1975 | Johnson |
| 3,958,569 A | 5/1976 | Vosburgh |
| 4,068,312 A | 1/1978 | Ledesma |
| 4,088,130 A | 5/1978 | Applegate |
| 4,136,404 A | 1/1979 | Lange |
| 4,169,467 A | 10/1979 | Rabischong et al. |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,769 A | 5/1983 | Erichsen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,493,316 A | 1/1985 | Reed et al. |
| 4,494,534 A | 1/1985 | Hutson |
| 4,503,846 A | 3/1985 | Martin |
| 4,520,804 A | 6/1985 | DiGeorge |
| 4,523,585 A | 6/1985 | Lamb et al. |
| 4,524,764 A | 6/1985 | Miller et al. |
| 4,554,913 A | 11/1985 | Womack et al. |
| D284,702 S | 7/1986 | Castillo |
| 4,599,748 A | 7/1986 | Garcia |
| 4,599,998 A | 7/1986 | Castillo |
| 4,603,690 A | 8/1986 | Skeen |
| 4,614,181 A | 9/1986 | Karlsson |
| 4,614,454 A | 11/1986 | Kassai |
| 4,620,532 A | 11/1986 | Housewerth |
| 4,621,624 A | 11/1986 | Rayboy |
| 4,628,916 A | 12/1986 | Lerman et al. |
| 4,633,867 A | 1/1987 | Kausek et al. |
| 4,665,905 A | 5/1987 | Brown |
| 4,681,097 A | 7/1987 | Pansiera |
| 4,697,583 A | 10/1987 | Mason et al. |
| 4,699,129 A | 10/1987 | Aeserude et al. |
| 4,715,363 A * | 12/1987 | Detty .................. A61F 5/0123 602/26 |
| 4,723,539 A | 2/1988 | Townsend |
| 4,732,143 A | 3/1988 | Kausek et al. |
| 4,753,240 A | 6/1988 | Sparks |
| D298,568 S | 11/1988 | Womack et al. |
| 4,791,916 A | 12/1988 | Paez |
| 4,802,372 A | 2/1989 | Harrod et al. |
| 4,803,975 A | 2/1989 | Meyers |
| 4,821,707 A | 4/1989 | Audette |
| 4,854,308 A | 8/1989 | Drillio |
| 4,856,501 A | 8/1989 | Castillo et al. |
| 4,886,054 A | 12/1989 | Castillo et al. |
| 4,890,607 A | 1/1990 | Townsend |
| 4,938,207 A | 7/1990 | Vargo |
| 4,940,044 A | 7/1990 | Castillo |
| 4,961,416 A | 10/1990 | Moore et al. |
| 4,964,402 A | 10/1990 | Grim et al. |
| 4,966,133 A | 10/1990 | Kausek |
| 4,986,264 A | 1/1991 | Miller |
| 4,991,571 A | 2/1991 | Kausek |
| 5,000,169 A | 3/1991 | Swicegood et al. |
| 5,005,565 A | 4/1991 | Fratesi |
| 5,022,391 A | 6/1991 | Weidenburner |
| 5,025,782 A | 6/1991 | Salerno |
| D318,736 S | 7/1991 | Castillo |
| 5,031,606 A | 7/1991 | Ring, Sr. |
| 5,038,763 A | 8/1991 | Wiggins |
| 5,038,765 A | 8/1991 | Young et al. |
| 5,062,858 A | 11/1991 | Broeck et al. |
| 5,063,916 A | 11/1991 | France et al. |
| 5,072,970 A | 12/1991 | Dandy, III et al. |
| 5,078,127 A | 1/1992 | Daneman et al. |
| 5,107,823 A | 4/1992 | Fratesi |
| 5,121,742 A | 6/1992 | Engen |
| 5,131,684 A | 7/1992 | Dandy, III et al. |
| 5,131,685 A | 7/1992 | Dandy, III et al. |
| 5,135,469 A | 8/1992 | Castillo |
| 5,168,865 A | 12/1992 | Radcliffe et al. |
| 5,222,733 A | 6/1993 | Brunty |
| 5,230,696 A | 7/1993 | Silver et al. |
| 5,230,697 A | 7/1993 | Castillo et al. |
| 5,259,832 A | 11/1993 | Townsend |
| 5,288,287 A | 2/1994 | Castillo et al. |
| D346,028 S | 4/1994 | Lengyel |
| 5,333,604 A | 8/1994 | Green et al. |
| 5,334,135 A | 8/1994 | Grim et al. |
| 5,356,370 A | 10/1994 | Fleming |
| 5,372,572 A | 12/1994 | Tamagni |
| 5,376,134 A | 12/1994 | Biedermann |
| RE34,818 E | 1/1995 | Daneman et al. |
| D357,070 S | 4/1995 | Castillo |
| 5,403,002 A | 4/1995 | Brunty |
| 5,443,444 A | 8/1995 | Pruyssers |
| 5,445,602 A | 8/1995 | Grim et al. |
| D367,536 S | 2/1996 | Kilbey |
| 5,490,822 A | 2/1996 | Biedermann |
| D370,261 S | 5/1996 | Kilbey |
| D370,533 S | 6/1996 | Kilbey |
| 5,554,104 A | 9/1996 | Grim |
| 5,641,322 A | 6/1997 | Silver et al. |
| 5,658,243 A | 8/1997 | Miller et al. |
| 5,662,596 A | 9/1997 | Young |
| 5,674,188 A | 10/1997 | Young |
| 5,695,452 A | 12/1997 | Grim et al. |
| 5,713,837 A | 2/1998 | Grim et al. |
| 5,716,335 A | 2/1998 | Iglesias et al. |
| 5,741,221 A | 4/1998 | Wetz et al. |
| 5,743,865 A | 4/1998 | Townsend |
| 5,766,140 A | 6/1998 | Tillinghast, III et al. |
| 5,772,618 A | 6/1998 | Mason et al. |
| 5,782,780 A | 7/1998 | Mason et al. |
| 5,792,084 A | 8/1998 | Wilson et al. |
| 5,794,261 A | 8/1998 | Hefling |
| 5,807,294 A | 9/1998 | Cawley et al. |
| 5,823,931 A | 10/1998 | Gilmour |
| 5,865,777 A | 2/1999 | Detty |
| 5,891,071 A | 4/1999 | Stearns et al. |
| 5,921,946 A | 7/1999 | Tillinghast et al. |
| 5,951,504 A | 9/1999 | Iglesias et al. |
| D416,624 S | 10/1999 | Nauert |
| 6,001,075 A | 12/1999 | Clemens et al. |
| 6,024,712 A | 2/2000 | Iglesias et al. |
| 6,027,466 A | 2/2000 | Diefenbacher et al. |
| 6,074,355 A | 6/2000 | Bartlett |
| D431,295 S | 9/2000 | Rothenburg |
| 6,129,689 A | 10/2000 | Dibello |
| D433,756 S | 11/2000 | Castillo |
| 6,205,583 B1 | 3/2001 | Beland |
| RE37,297 E | 7/2001 | Smith, III |
| 6,290,664 B1 | 9/2001 | Nauert |
| D451,644 S | 12/2001 | Fujimoto et al. |
| 6,393,610 B1 | 5/2002 | Parks |
| 6,402,711 B1 | 6/2002 | Nauert |
| D463,886 S | 10/2002 | Cantu, Jr. |
| 6,461,318 B2 | 10/2002 | Freeman et al. |
| 6,464,657 B1 | 10/2002 | Castillo |
| 6,500,139 B1 * | 12/2002 | Townsend ............. A61F 5/0123 602/26 |
| 6,540,709 B1 | 4/2003 | Smits |
| 6,676,617 B1 | 1/2004 | Miller |
| 6,689,080 B2 | 2/2004 | Castillo |
| 6,736,567 B1 | 5/2004 | Dibello |
| 6,740,054 B2 | 5/2004 | Stearns |
| 6,752,775 B2 | 6/2004 | Seligman et al. |
| 6,793,641 B2 | 9/2004 | Freeman et al. |
| 6,796,951 B2 | 9/2004 | Freeman et al. |
| D501,690 S | 2/2005 | Chen |
| 6,875,187 B2 | 4/2005 | Castillo |

(56) References Cited

U.S. PATENT DOCUMENTS

| | | | |
|---|---|---|---|
| 6,878,126 B2 | 4/2005 | Nelson et al. | |
| D504,981 S | 5/2005 | Vanderhoef | |
| 6,890,314 B2 | 5/2005 | Seligman | |
| 6,988,999 B1 | 1/2006 | Lin | |
| D517,248 S | 3/2006 | Castillo et al. | |
| 7,044,925 B2 | 5/2006 | Castillo et al. | |
| 7,059,329 B2 | 6/2006 | Mason et al. | |
| 7,189,212 B2 | 3/2007 | Popp et al. | |
| 7,235,058 B2 | 6/2007 | Doty et al. | |
| 7,311,686 B1 | 12/2007 | Iglesias et al. | |
| 7,311,687 B2 | 12/2007 | Hoffmeier et al. | |
| D558,884 S | 1/2008 | Ingimundarson et al. | |
| D577,828 S | 9/2008 | Ingimundarson et al. | |
| 7,507,215 B2 | 3/2009 | Ryan | |
| 7,534,219 B2 | 5/2009 | Stearns | |
| 7,544,174 B2 | 6/2009 | Nathanson | |
| 7,578,799 B2 | 8/2009 | Thorsteinsson et al. | |
| 7,662,119 B2 | 2/2010 | DeToro et al. | |
| 7,682,322 B2 | 3/2010 | Engelman | |
| 7,699,798 B2 | 4/2010 | Coligado | |
| 7,722,555 B2 | 5/2010 | Doty et al. | |
| 7,749,183 B2 | 7/2010 | Ingimundarson et al. | |
| 7,762,972 B2 | 7/2010 | Cho | |
| 7,811,242 B2 | 10/2010 | Seligman | |
| 7,967,765 B2 | 6/2011 | Nathanson | |
| 7,985,193 B2 | 7/2011 | Thorsteinsson et al. | |
| 8,043,243 B2 | 10/2011 | Nathanson et al. | |
| 8,048,013 B2 | 11/2011 | Ingimundarson et al. | |
| 8,062,242 B2 | 11/2011 | Ceriani et al. | |
| 8,202,325 B2 | 6/2012 | Albrecht-Laatsch et al. | |
| 8,287,476 B2 | 10/2012 | Bettiol | |
| 8,292,838 B2 | 10/2012 | Ingimundarson et al. | |
| 8,795,212 B2 | 8/2014 | Seligman | |
| 8,864,692 B2 | 10/2014 | Ingimundarson et al. | |
| 8,939,924 B1 | 1/2015 | Paulos | |
| 8,979,782 B2 | 3/2015 | Romo et al. | |
| 9,125,730 B2 | 9/2015 | Ingimundarson et al. | |
| 9,220,625 B2 | 12/2015 | Ingimundarson et al. | |
| 9,333,107 B2 * | 5/2016 | Potter | A61H 3/00 |
| 9,345,605 B2 | 5/2016 | Dunn et al. | |
| 9,668,903 B2 | 6/2017 | Hsu et al. | |
| 9,788,986 B2 | 10/2017 | Dunn | |
| 10,588,770 B2 | 3/2020 | Brookover et al. | |
| 2002/0107462 A1 | 8/2002 | Freeman et al. | |
| 2002/0107464 A1 | 8/2002 | Castillo | |
| 2002/0183674 A1 | 12/2002 | Castillo | |
| 2004/0002674 A1* | 1/2004 | Sterling | A61F 5/0123 602/26 |
| 2004/0019949 A1 | 2/2004 | Crockett | |
| 2004/0054307 A1 | 3/2004 | Mason et al. | |
| 2004/0097859 A1 | 5/2004 | Stearns | |
| 2004/0167452 A1 | 8/2004 | Mason et al. | |
| 2005/0148915 A1 | 7/2005 | Nathanson et al. | |
| 2005/0148918 A1 | 7/2005 | Nathanson | |
| 2005/0165338 A1 | 7/2005 | Iglesias et al. | |
| 2005/0192523 A1 | 9/2005 | Knecht et al. | |
| 2006/0009722 A1 | 1/2006 | Seligman | |
| 2006/0100561 A1 | 5/2006 | Gilmour | |
| 2006/0135901 A1 | 6/2006 | Ingimundarson et al. | |
| 2006/0135903 A1 | 6/2006 | Ingimundarson et al. | |
| 2006/0167394 A1 | 7/2006 | Ceriani et al. | |
| 2006/0167396 A1 | 7/2006 | Berger | |
| 2006/0173392 A1 | 8/2006 | Turrini et al. | |
| 2006/0287624 A1 | 12/2006 | Popp et al. | |
| 2007/0225824 A1 | 9/2007 | Einarsson | |
| 2007/0293798 A1 | 12/2007 | Hu et al. | |
| 2008/0108922 A1 | 5/2008 | Castillo et al. | |
| 2008/0188784 A1 | 8/2008 | Ceriani et al. | |
| 2009/0030356 A1 | 1/2009 | Maloney | |
| 2009/0182254 A1 | 7/2009 | Cho | |
| 2009/0299244 A1 | 12/2009 | Chiang et al. | |
| 2010/0049108 A1 | 2/2010 | Paez | |
| 2010/0286579 A1 | 11/2010 | Bettiol | |
| 2011/0152736 A1 | 6/2011 | Ng | |
| 2012/0059296 A1 | 3/2012 | Kompa | |
| 2012/0271211 A1 | 10/2012 | Bledsoe | |
| 2013/0331754 A1 | 12/2013 | Dunn et al. | |
| 2014/0094351 A1* | 4/2014 | Cersonsky | A63B 21/15 482/115 |
| 2014/0207040 A1 | 7/2014 | Ingimundarson et al. | |
| 2014/0330393 A1 | 11/2014 | Ward et al. | |
| 2015/0038889 A1* | 2/2015 | Mason | A61B 17/132 24/68 D |
| 2015/0223958 A1 | 8/2015 | Dunn | |
| 2015/0267450 A1 | 9/2015 | Chiang | |
| 2015/0374530 A1 | 12/2015 | Bosshard et al. | |
| 2016/0008157 A1 | 1/2016 | Brookover et al. | |
| 2016/0038327 A1* | 2/2016 | Mason | A61F 5/0123 602/16 |
| 2016/0058596 A1* | 3/2016 | Chiang | A61F 5/0123 602/16 |
| 2016/0143763 A1 | 5/2016 | Hsu et al. | |
| 2016/0278947 A1 | 9/2016 | Martin | |
| 2017/0110937 A1 | 4/2017 | Billings | |
| 2017/0119569 A1 | 5/2017 | Hsu et al. | |
| 2017/0298981 A1 | 10/2017 | Asgeirsson | |
| 2018/0153711 A1 | 6/2018 | Hsu et al. | |

FOREIGN PATENT DOCUMENTS

| | | |
|---|---|---|
| EP | 0070411 A1 | 1/1983 |
| EP | 0327286 A2 | 8/1989 |
| EP | 0382976 A1 | 8/1990 |
| EP | 0413424 A1 | 2/1991 |
| EP | 0454186 A2 | 10/1991 |
| EP | 0546330 A1 | 6/1993 |
| EP | 0615734 A1 | 9/1994 |
| EP | 0693276 A1 | 1/1996 |
| EP | 1010409 A1 | 6/2000 |
| EP | 1388330 A1 | 2/2004 |
| EP | 1639970 A2 | 3/2006 |
| EP | 2345393 A1 | 7/2011 |
| EP | 2823792 A1 | 1/2015 |
| GB | 190626961 A | 4/1907 |
| WO | 9014807 A1 | 12/1990 |
| WO | 9939668 A1 | 8/1999 |
| WO | 0110360 A1 | 2/2001 |
| WO | 2004078078 A1 | 9/2004 |
| WO | 2009092798 A1 | 7/2009 |
| WO | 2014067698 A1 | 5/2014 |
| WO | 2015157723 A1 | 10/2015 |
| WO | 2016100791 A1 | 6/2016 |
| WO | 2017075143 A1 | 5/2017 |

OTHER PUBLICATIONS

Innovation Sports, Products, Knee, OTS "Aspire", 1 page, available at least as early as Feb. 12, 2007.
Innovation Sports, Products, Knee, OTS "Edge", 1 page, available at least as early as Feb. 12, 2007.
Innovation Sports, Products, Knee, OTS "Morph", 1 page, available at least as early as Feb. 12, 2007.
Innovation Sports, Products, Knee, Ots "PCL", 1 page, available at least as early as Feb. 12, 2007.
International Search Report from PCT Application No. PCT/US2020/024984, Aug. 18, 2020.

* cited by examiner

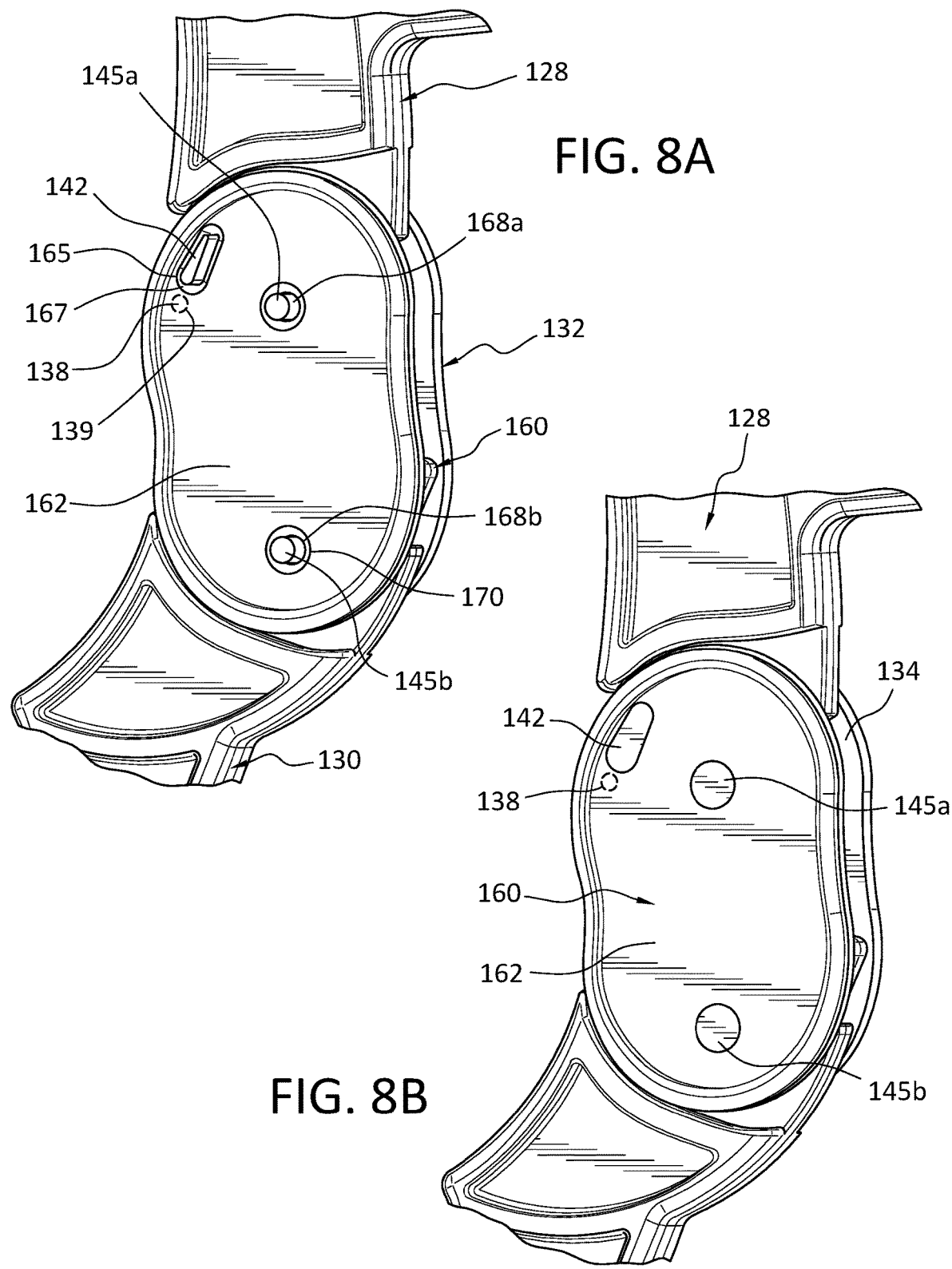

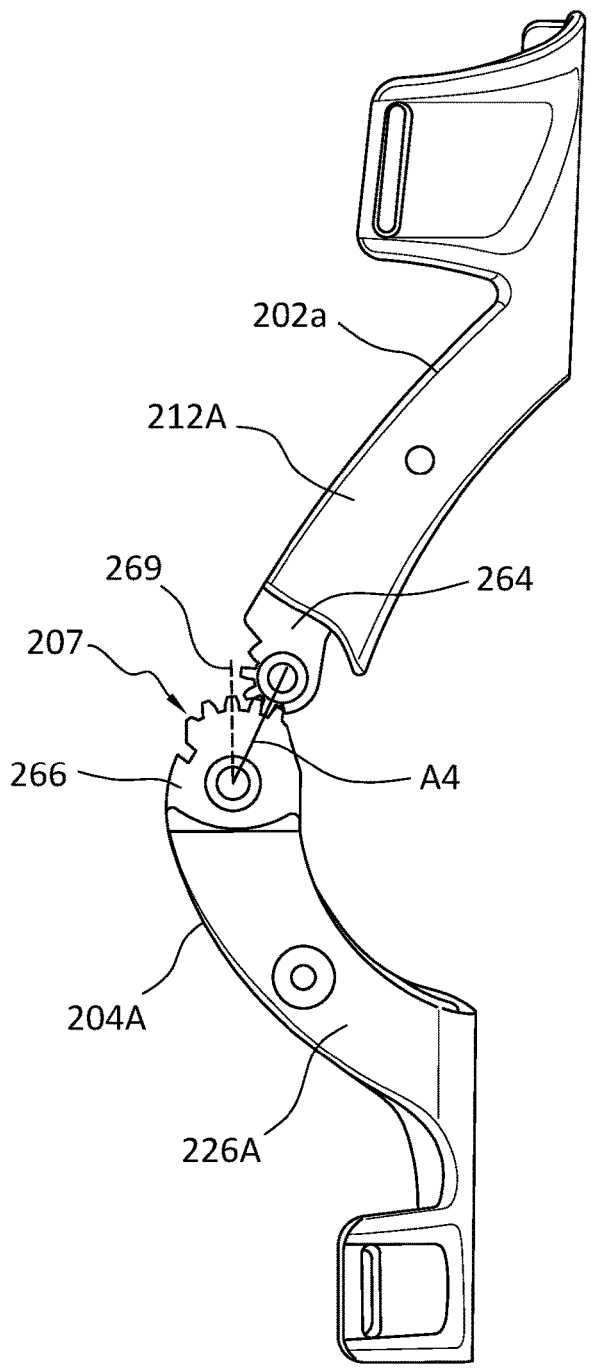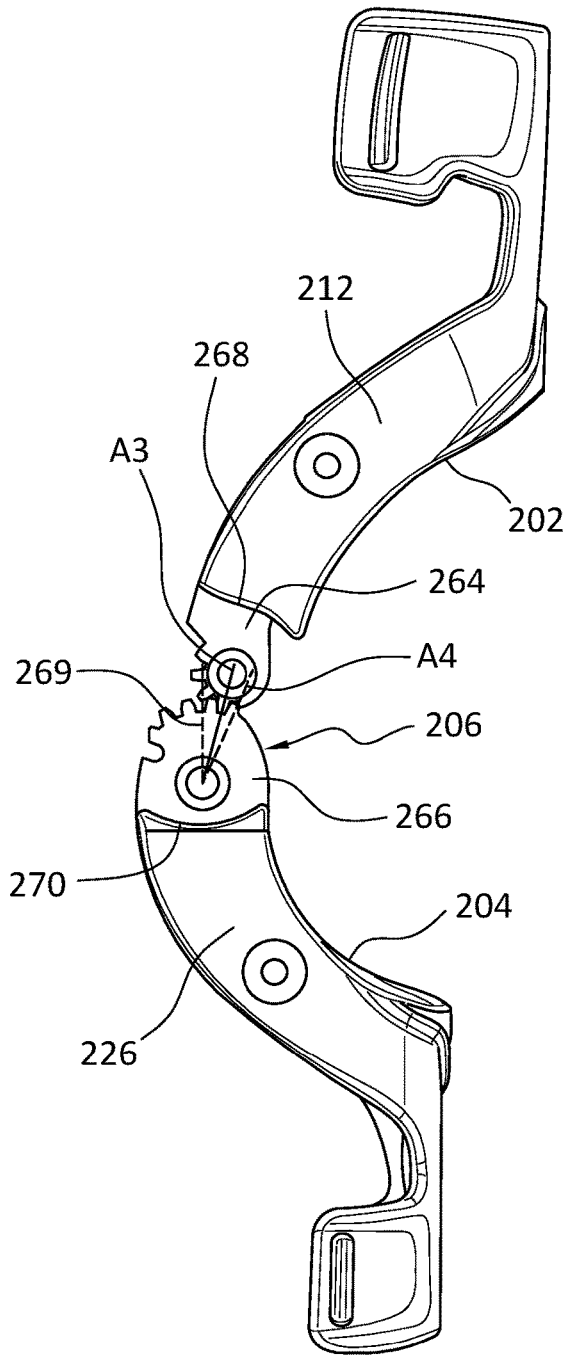
FIG. 10B
FIG. 10A

HINGE ASSEMBLY FOR AN ORTHOPEDIC DEVICE

CROSS-REFERENCE TO RELATED APPLICATION

This application incorporates by reference the entirety of US patent application publication 2017/0119569, published May 4, 2017, and owned by the assignee of this application.

TECHNICAL FIELD

The disclosure relates to a hinge assembly for use with an orthopedic or prosthetic device.

BACKGROUND

Many orthopedic devices include hinges that support joints and control and limit joint movements. Such joints can include the knee, elbow, shoulder, hip, ankle, and wrist joints.

The knee joint comprises two joints, lateral and medial, between the femur and tibia, and one arthrodial joint between the patella and femur. The primary movements of the knee comprise flexion (i.e., rearward rotational movement of the tibia relative the femur), and extension (i.e., forward rotational movement of the tibia relative the femur).

The flexion and extension movements of the knee joint are not pivotal movements about a fixed axis. Instead, during flexion, the axis around which movement takes place shifts backward, and during extension, the axis shifts forward. This movement differs from a more typical hinge joint, such as an elbow, where the axis of rotation does not shift during movement.

As full extension is reached, the tibia rotates inward or rearward, and the joint orients in a "locked" position with the ligaments taut. This orientation gives the joint greater stability in the extended position. As flexion initiates, the tibia initially lowers or moves downwardly with small external rotation of the tibia unlocking the joint and subsequently, the tibia rotates or rolls about the joint to full flexion. The initial unlocking of the knee joint during flexion precedes actual full rotation of the knee.

Because of the complexity associated with knee movement, a knee-brace hinge must be able to simulate the complex anatomical movements of the knee, including the shifting of the axis as described above. Incorporating such movement into the hinge is useful, as the knee brace must optimally support the knee joint of its user throughout the normal range of motion and use for increased comfort, compliance, and efficacy. The knee-brace hinge can also assist in applying loads to the knee that will improve in the healing of injuries or relief from osteoarthritic complications and improve comfort for and compliance by a user.

Many attempts have been made to make a knee-brace hinge that is both anatomically correct and robust, yet such attempts have resulted in hinges that are relatively complex, expensive, and limited in control and movement. For instance, known geared hinges are robust and easily manufactured but produce only one motion relationship that is neither anatomical nor provides loads to heal a knee injury. Other known hinges, such as traditional four-bar hinges, may produce a more natural knee movement but are very complicated in design, are costly, and provide limited control over the motion of the knee brace. This arrangement increases the cost and complexity of the use and manufacture of hinges.

As such, there is currently an absence of and a need for an improved hinge assembly that provides anatomically accurate motion and support to a knee compared to existing geared hinges while reducing the cost, complexity, and limited control of existing four-bar hinge solutions.

There is further a need for a hinge assembly that is both easily manufactured and robust, and capable of producing different motion relationships and loading profiles on a knee brace.

SUMMARY

Hinge assembly embodiments described herein are adapted to more accurately imitate anatomical knee motion and create desired loads on the knee more simply and effectively than in the prior art. The hinge assembly can be adapted for use with orthopedic devices and prosthetic devices and other devices and other joints as suitable.

According to an embodiment of a hinge assembly for an orthopedic device of the disclosure, the hinge assembly defines a motion path formed by variable translation in a polycentric hinge. The hinge assembly includes a first hinge arm including a first end portion and a second hinge arm including a second end portion. The first and second end portions are arranged to engage one another and have differently sized radii relative to one another. Each of the first and second hinge arms has a plurality of teeth arranged to interact with corresponding teeth on the other hinge arm. For instance, the first hinge arm has a first plurality of teeth corresponding to and arranged to cooperate with a second plurality of teeth defined by the second hinge arm. In embodiments, the first hinge arm cooperates with the second hinge arm only about the first and second gear profiles or end portions.

The first and second end portions including the radii and teeth can be selected or varied to allow the second hinge arm to travel along a defined motion path relative to the first hinge arm, for example, to simulate accurate anatomical movement. The defined motion path can include a complex hinge motion. A "complex hinge motion" as defined herein is when at least one of the hinge arms translates relative to the other in a variable manner. For instance, a complex hinge motion can include translation of the second hinge arm relative to the first hinge arm to generally match anatomical knee motion and to apply loads to the knee.

The hinge assembly may be a polycentric hinge with axes of rotation offset from each other to form a defined motion path that more accurately simulates the anatomical movement of the knee. The complex hinge motion may cause the second hinge arm, corresponding in embodiments to the lower leg, to move backward relative to the first hinge arm, corresponding in embodiments to the upper leg, during rotation. The interaction between the first and second end portions provides robust control over the relative motion between the hinge arms, allowing for many functional designs, improved customization for individual users' needs, and improved accuracy of simulating the natural anatomical movement of a human knee.

The hinge assembly embodiments according to the present disclosure further allow for a simpler construction and operation than the four-bar hinges of the prior art, resulting in hinges easier to use and construct, more cost-effective to produce, more robust, and more intuitive to design. The hinge assembly embodiments of the disclosure attain the simplicity, cost-effectiveness, and structural advantages, such as being of lighter weight, of existing polycentric hinges and the anatomical advantages of existing four-bar hinges while mitigating the drawbacks of both.

Embodiments of the disclosure further provide an improved extension stop for a hinge assembly in an orthopedic device. Whereas existing extension stops may be arranged simply for interacting with a corresponding surface of a hinge arm to arrest flexion or extension past a certain degree of motion, usually with a "hard stop," there is a need for extension stops that provide improved comfort to a user during use and cushioning for a hinge assembly against hard impacts that may damage components of the hinge. In embodiments, an extension stop may be provided with a soft or resilient extension stop that improves comfort by compressing before contact between a hinge arm and the extension stop. This arrangement slows the rate of contact and provides a softer landing than existing extension stops, and offers means for damping the hinge assembly as it approaches a predetermined extension angle.

The extension stop installs without disassembly of the hinge assembly, and advantageously may be replaced by extension stops each defining a different predetermined extension angle. The extension stop may be secured to the hinge assembly without an external tool due to cooperating locking features with the hinge assembly. It may be retained with the hinge assembly based on such cooperating locking features. Additional securing means may be provided by a fastener accessible external of or to the hinge assembly.

Embodiments also provide an improved flexion stop that may be inserted and removed without disassembly of the hinge assembly. The flexion stop has locking features cooperating with the hinge assembly to lock the flexion stop relative to the hinge assembly, but such locking features permit easy removal of the flexion stop without disassembly of the hinge assembly. Embodiments enable installation and removal of the flexion stop without tool or fasteners, as the locking features are inherent in constructing the flexion stop and hinge assembly.

According to the features of the hinge assembly, the hinge assembly may be completely constructed from polymeric materials. While prior art hinges may mix polymeric, metal and composite materials, constructing the hinge assembly facilitates the hinge assembly to be formed as part of frame members of an orthopedic device because the hinge assembly may be injection molded or otherwise formed monolithically as part of hinge arms.

Frame members or arms of the orthopedic device from which the hinge assembly depends may be constructed continuously with the material as teeth that mesh together in operating the polycentric hinge. While a four-bar hinge is often understood to better mimic the motion of a knee, an offset arrangement of axes about which hinge arms rotate approximates the same motion of a four-bar hinge in a polycentric hinge, which enables the hinge assembly to be formed with the frame components in simplified form. The hinge assembly embodiments attain the advantageous features of polycentric hinges and four-bar hinges while mitigating the respective drawbacks of each.

BRIEF DESCRIPTION OF THE DRAWINGS

These and other features, aspects, and advantages of the present disclosure will become better understood regarding the following description, appended claims, and accompanying drawings.

FIG. 8A is a perspective view of the hinge assembly in FIG. 7A with the outer plate covering the hinge assembly and in an unsecured configuration to the inner plate.

FIG. 8B is a perspective view of the hinge assembly in FIG. 8A with the outer plate in a secured configuration to the inner plate.

FIG. 10A is an elevational view of the orthopedic device of FIG. 9A having a hinge oriented at 15°.

FIG. 10B is an elevational view of a variation of the orthopedic device of FIG. 9A having a hinge oriented at 25°.

DETAILED DESCRIPTION OF VARIOUS EMBODIMENTS

A. Overview

Figure 1:
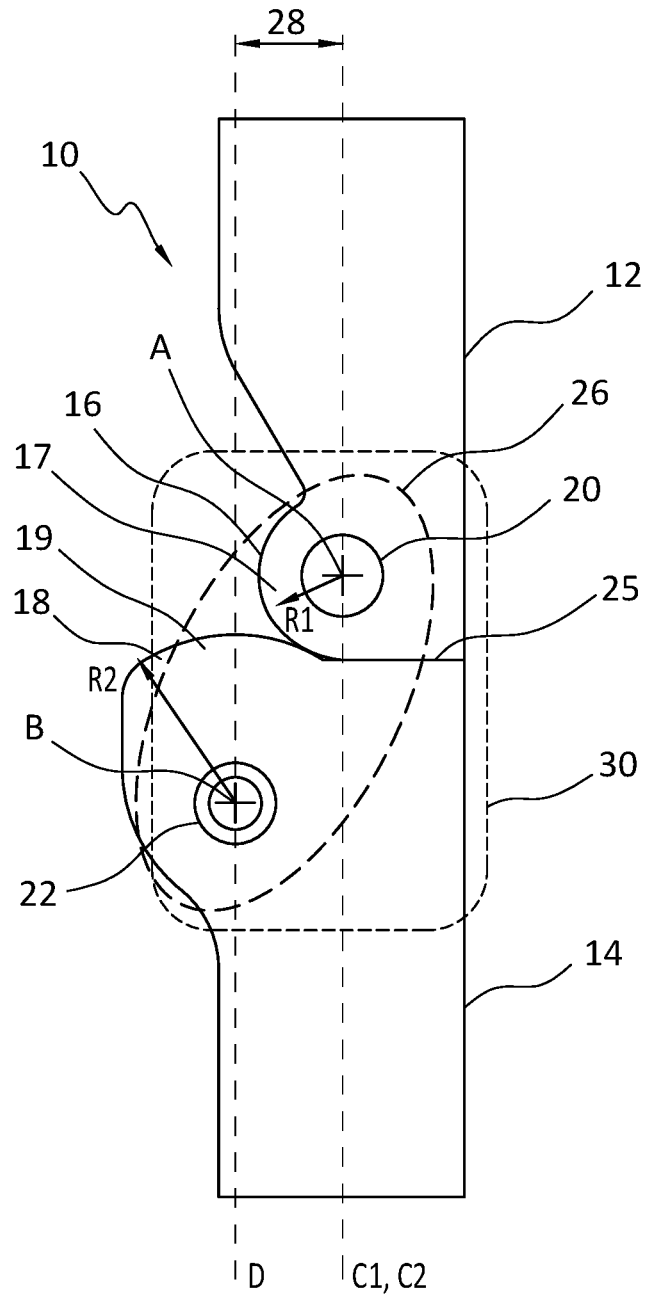
FIG. 1 is a schematic elevational view of a hinge assembly according to the disclosure.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

B. Environment and Context of Embodiments

Numerous orthopedic device embodiments and components (e.g., subshells and strap retainers) for use therewith are described herein, with particular focus given to braces and components directed to the knee joint and surrounding areas. The orthopedic brace embodiments may serve in protective, preventive or remedial capacities. While the orthopedic brace is described within the context of a preferred embodiment directed to securing the knee joint, many features described herein may be extended to orthopedic braces and components that secure other joints and body parts, such as the wrist, elbow, shoulder, ankle and neck.

The brace embodiments and components for use therewith may be dimensioned to accommodate different types, shapes, and sizes of human joints and appendages. In addition, embodiments may be modified to orient principal forces exerted by strap systems of the embodiments at any desirable location to secure the brace onto a leg to stabilize the knee.

The knee joint comprises two joints, lateral and medial, between the femur and tibia, and one arthrodial joint between the patella and femur. The primary movements of the knee comprise flexion, i.e., rearward rotational movement of the tibia relative to the femur, and extension, i.e., forward rotational movement of the tibia relative to the femur.

For explanatory purposes, each orthopedic brace embodiment or component thereof described may be divided into sections denoted by general anatomical terms for the human body. Such anatomical terms are provided to distinguish various elements of the brace embodiments from one another, but which are not to be considered to limit the scope of the invention.

Each term is used referring to a human leg, for example, which is divided in similar sections with a proximal-distal plane generally extending along with the meniscus of the knee between the femur and tibia. The terms "proximal" and "distal" generally refer to locations of the brace that correspond to the location of the leg relative to the point of attachment of the leg to the body. The terms "upper" and "lower" may be used in combination with "proximal" and "distal" to connote gradations in the location of "proximal" and "distal." The location at where the brace corresponds to the knee joint is used herein to generally delimit the proximal and distal sections of the brace.

The embodiments of the knee brace can also be considered to fall within "anterior" and "posterior" sections by an anterior-posterior plane. The anterior-posterior plane generally corresponds to the coronal or frontal plane of a human leg, which lies along the central longitudinal axis of a body. A posterior side or element is therefore located behind this anterior-posterior plane, whereas an anterior side or element is located in front of the anterior-posterior plane.

The terms "inwardly" or "inner" may be used herein to distinguish the side of the brace that may be directed to the interior side of the brace and specifically adjacent to the leg of the wearer of the brace. Contrariwise, the term "outwardly" or "outer" are used to denote the side of the brace that is opposite to the inwardly side.

The terms "medial" and "lateral" are relative terms that are generally understood as indicating location near the midsagittal plane or midline. Therefore, elements that are located near the midline are referred to as "medial," and those elements that are further from the midline are considered to be "lateral." The term "central" is used to denote the area along the midline of a joint, thereby dividing and sharing regions of the medial and lateral regions.

From these terms, the anterior section of the brace has these quadrants: (I) proximal-medial, (II) distal-medial, (III) distal-lateral, and (IV) proximal-lateral. The posterior section of the brace has these quadrants: (V) proximal-medial, (VI) distal-medial, (VII) distal-lateral, and (VIII) proximal-lateral. Structural members and features thereof will fall within one quadrant as referenced explicitly in relation to such quadrant, either in its entirety or partially.

The terms "rigid" and "flexible" may be used herein to distinguish characteristics of portions of the hinge or brace. The term "rigid" should denote that the frame is generally devoid of flexibility. Within the context of frame members or components that are "rigid," it should indicate that they may break if bent with sufficient force. But the term "flexible" should denote that features are capable of repeated bending. The word "resilient" is used to qualify such flexible features as generally returning to the initially molded shape without permanent deformation.

The anatomical and characteristic terms described are not intended to detract from the normal understanding of such words as readily understood by one of ordinary skill in the art of orthotics. The elements of the embodiments described should embrace embodiments that generally correspond to the aforementioned anatomical sections. It is understood that the elements of the brace embodiments described may deviate from falling exactly within the confines of the aforementioned anatomical sections.

C. Various Embodiments and Components for Use Therewith

Numerous hinge assembly embodiments are described herein, with particular focus given to the knee joint and surrounding areas. The hinge assembly embodiments may serve in protective, preventive or remedial capacities. While the hinge assembly is described within the context of a preferred embodiment directed to treating the knee, many features described may be extended to orthopedic devices and components that secure other joints and body parts. It should be appreciated that the hinge assembly embodiments may be dimensioned to accommodate different types, shapes, and sizes of human joints and appendages. It should also be appreciated that the hinge assembly can be adapted for prosthetic devices, medical devices, or other devices.

The hinge assembly embodiments may be formed from a rigid polymeric material or a fiber-reinforced polymeric material, for example, in monolithic construction with other components, such as a frame, strut, or otherwise, of an orthopedic, prosthetic, medical, or other devices. Due to the simplified construction, as will be apparent in the exemplary embodiments, other materials may likewise form the hinge assembly such as metals or composites, and the embodiments are not limited to only polymeric materials. The cost and complexity of producing and using hinge assemblies may be reduced by constructing a hinge assembly according to the embodiments of the disclosure.

In the preferred embodiments, as the hinge assembly is formed from the same materials as frame components of the orthopedic device, as opposed to the orthopedic device being an assembly of components, the hinge assembly can be formed simultaneously with frame elements of an orthopedic device, greatly simplifying manufacture of an orthopedic device and improving the structural stability. Structurally, the hinge assembly may be continuous and monolithic with hinge arms extending from the frame and may be formed from the same material as the hinge arms, so the interlocking ends of the hinge assembly are an extension of the frame itself rather than additional and inserted parts. Providing the hinge components separately from other frame components is also contemplated.

As understood below, the hinge assembly is a "polycentric" hinge commonly understood in the art of orthopedic braces as including a pair of rigid support arms having cooperating, interlocking proximal ends, a pair of pivot pins and a hinge plate. The arms are rotatably coupled at their proximal ends to the hinge plate through the pivot pins and are rotatable between an adjustable extension position and an adjustable flexion position. An example of a polycentric hinge is described in U.S. Pat. No. 5,443,444, granted Aug. 22, 1995, and an example of a four-bar hinge is described in U.S. Pat. No. 8,979,782, granted on Mar. 17, 2015, each of which is incorporated herein by reference.

FIG. 1 depicts a hinge assembly 10 including a first hinge arm 12 having a first longitudinal axis C1. The first hinge arm 12 defines a first end portion 16 having a first opening 20 having a first axis A. The first axis A may be orthogonal to the first longitudinal axis C1. The first hinge arm 12 is pivotable about the first axis A. The hinge assembly 10 includes a second hinge arm 14 having a second longitudinal axis C2. The second hinge arm 14 defines a second end portion 18 having a second opening 22 defining a second axis B and the second hinge arm 14 is pivotable about the second axis B. Like the first axis A, the second axis B may be orthogonal to the second longitudinal axis C2.

Suitable pins or pin elements may be provided in the first and second openings 20, 22 in and/or about which the first and second hinge arms 12, 14 pivot, and such pins generally remain in a fixed spatial relationship while the first and second hinge arms 12, 14 rotate.

As shown in the exemplary embodiment of FIG. 1, the first and second longitudinal axes C1, C2 are coaxial when in an idealized extension configuration. The second opening 22 is arranged along a third longitudinal axis D parallel to the first and second longitudinal axes C1, C2 and is offset therefrom by a distance 28. This arrangement is unlike conventional polycentric hinges wherein the openings would be arranged along the same longitudinal axis.

Because of the offset or distance 28, the hinge assembly 10 can better mimic the corresponding rotational motion of a four-bar hinge throughout a defined motion path and without the complex constructions of an existing four-bar hinge. FIG. 1 exemplifies how a four-bar hinge 26 would connect to the first and second end portions 16, 18, which would not engage one another but rather would have a spatial rotational relationship relative to one another.

Unlike in a conventional four-bar hinge, the first end portion 16 and the second end portion 18 preferably define first and second geared profiles 17, 19, respectively, arranged to cooperate with one another, as in a conventional polycentric hinge. Yet the first and second end portions 16, 18 of embodiments according to the disclosure are offset as described above to mimic a four-bar hinge. An extension stop may be formed at or as an interface 25 defined by cooperating surfaces of the first and second hinge arms 12, 14. A hinge plate 30 is used to retain the first and second end portions 16, 18 connected, aside from their preferable geared profiles.

The first and second geared profiles 17, 19, respectively, of each the first end portion 16 and the second end portion 18 preferably form an identical amount or number of teeth. The teeth of the first and second end portions 16, 18 are preferably similarly sized. The teeth may be formed only about a limited periphery of the first and second geared profiles 17, 19.

The limited periphery forming the teeth may have a uniform radius or curvature about the respective end portion or geared profile. In contrast, adjacent peripheral portions may have a different configuration or different curvatures, or irregularly dimensioned profiles. In embodiments, the first end portion 16 may have a first radius R1 smaller than a second radius R2 of the second end portion 18, at least about the limited periphery of the first and second geared profiles 17, 19. The difference between and dimensions of radii of corresponding end portions may help define an anatomically accurate define motion path and may take any suitable configuration or shape.

The offset or distance 28 among the first and second end portions 16, 18 enables the hinge 10 to provide a motion that better mimics or approximates the natural movement of a knee over a conventional polycentric hinge. When the hinge assembly 10 is in the idealized extension configuration of FIG. 1, the second axis B is offset and arranged along with the third longitudinal axis D, and the third longitudinal axis D is parallel and offset relative to the second longitudinal axis C2, enabling the second hinge arm 14 to travel through the desired curvature and/or path relative to the first arm 12 when the hinge 10 is bent in flexion. Unlike the second axis B, the first axis A is preferably centrally arranged on the first end portion 16. The second axis B, by contrast, is depicted as an offset from a center of the second end portion 18. The depicted arrangement of the first and second axes A, B, is by no means limiting.

Figure 2:
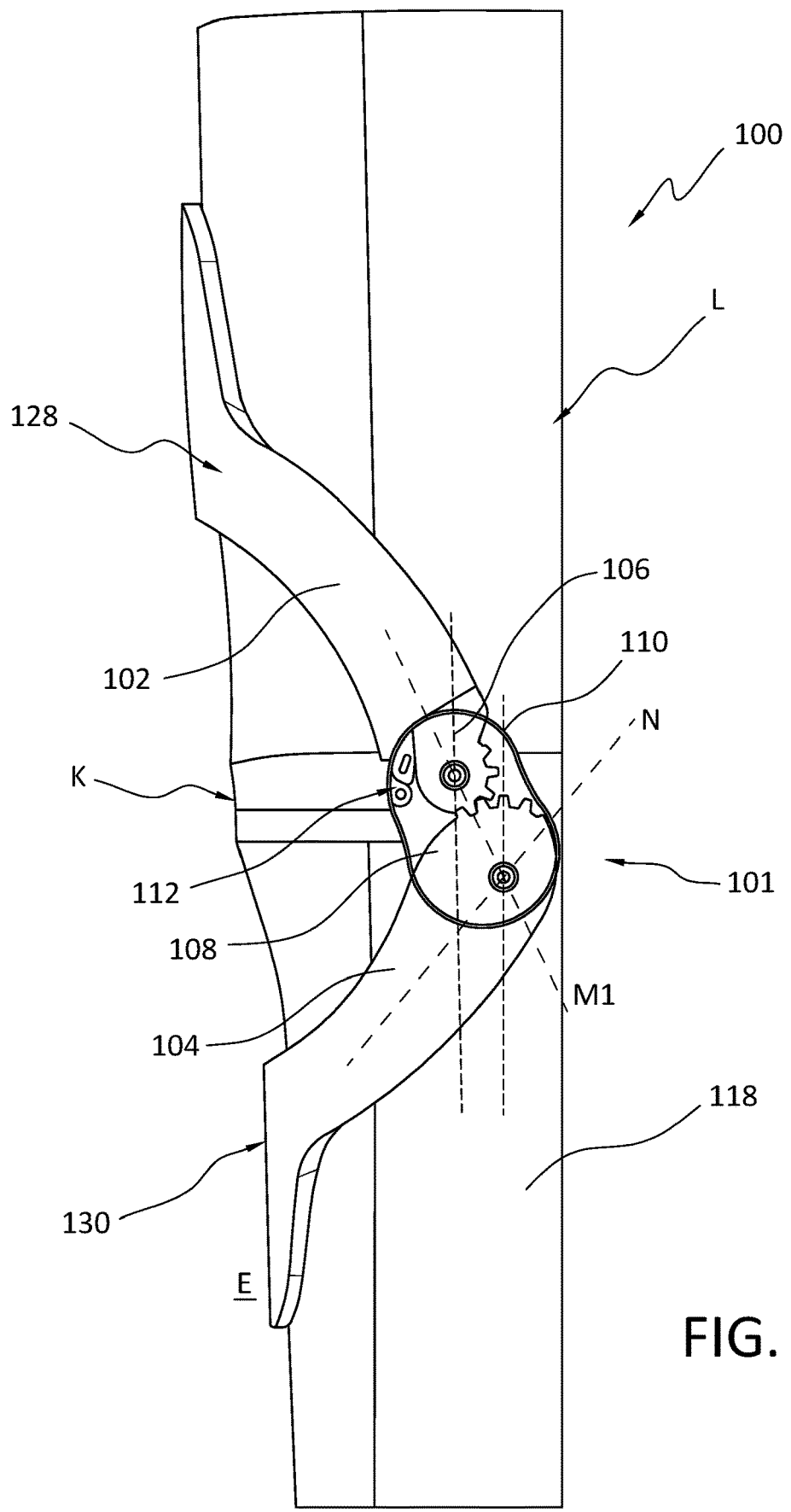
FIG. 2 is an exemplary elevational view of another hinge assembly in an orthopedic device on a leg according to the disclosure.

FIG. 2 shows an orthopedic device or knee brace embodiment 100 having a hinge assembly 101 similar to the hinge assembly 10 of FIG. 1 and cooperating with a sleeve 118. A first hinge arm 102 is generally fixed relative to a user's femur and extends from a first frame member 128, such as a frame member about an upper leg L, and has a first longitudinal axis M1. The first hinge arm 102 defines a first end portion 106. A second hinge arm 104 may extend from a second frame member 130 about a lower leg and is arranged to rotate and translate relative to the first hinge arm 102 during gait, and has a second longitudinal axis M2. The movement of the second hinge arm 104 about or relative to the upper hinge arm 102 is based at least in part on the force applied to a second end portion 108 of the second hinge arm 104 during gait relative to an instantaneous center of rotation "ICoR" of the second hinge arm 104.

The ICoR of the second hinge arm 104 is a point about which the second hinge arm 104 rotates as the hinge assembly 101 moves between extension and knee flexion. As in the embodiment of FIG. 1, the first and second hinge arms 102, 104 may comprise openings offset relative to each other by a distance 126. Whereas an opening of the first hinge arm 102 may be aligned along with the first longitudinal axis M1, an opening of the second hinge arm 104 may be aligned along with a third longitudinal axis N distinct from the second longitudinal axis M2 of the second hinge arm 104. By being spaced apart from the longitudinal axes M1, M2, when in an idealized extension configuration, the hinge assembly 101 assists in defining a dynamic ICoR that better imitates the natural movement of the knee joint.

Figure 3:
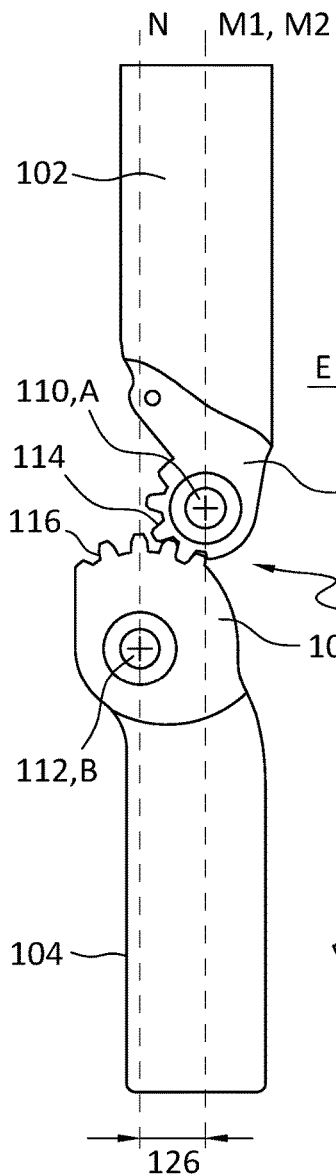
FIG. 3 is a schematic view of the hinge assembly of FIG. 2 in an idealized full extension configuration whereby both the first and second hinge arms are aligned.

The location of the ICoR of the second hinge arm 104 can depend on the relative sizes, profiles, and/or arrangements between the first and second end portions 106, 108, and the position of corresponding first and second teeth 114, 116, as seen in FIG. 3. In use, the ICoR of the second hinge arm 104 shifts as the user's knee K moves through extension E and flexion F because the point of contact between the first teeth 114 and second teeth 116 moves as the second hinge arm 104 rotates relative to the first hinge arm 102, as illustrated from comparing the hinge assembly 101 in extension E in FIG. 3 to the same hinge assembly 101 in flexion F in FIG. 4. The hinge assembly 101 may further comprise an extension stop 112 arresting extension past a desired degree. The extension stop 112 may be arranged on or proximate a plate 110 enclosing the hinge assembly 101 and facilitating rotation and operation thereof.

The ICoR moves along an ICoR path. An ICoR path is generally a path along which an ICoR of an object moves while the object is rotating. As the ICoR of the second hinge arm 104 shifts, the position of the second hinge arm 104 relative to the first hinge arm 102 shifts, resulting in translational movement of the second hinge arm 104 relative to the first hinge arm 102 as it rotates. The ICoR of the second hinge arm 104 and its corresponding frame member in an orthopedic device 100 may be arranged to imitate the complex movement of a lower leg relative to an upper leg during flexion and extension.

The profiles of the first and second end portions 106, 108 along with the first and second teeth 114, 116 at least in part define the movement of the ICoR of the second hinge arm 104 relative to the first hinge arm 102. The profiles of the first and second end portions 106, 108 along with the first and second teeth 114, 116 can be selected or varied as needed to match a defined motion path, including a complex hinge motion, e.g., when at least one of the hinge arms translates relative to the other in a non-linear or variable manner. This beneficially allows the hinge assembly 101 to be adapted to imitate anatomical knee motion and/or apply loads on the knee that may improve healing of injuries, relief from osteoarthritic complications, or correction of deformities. This is advantageous over traditionally geared hinges, which, while being relatively simple and cost-effective to manufacture, produce only one simple motion relationship that is neither anatomical nor provides loads to heal a knee injury.

In the illustrated embodiment, a first profile of the first end portion 106 generally follows a segment of a circle and is larger than a second profile of the second end portion 108, which also generally follows a segment of a circle. As the second hinge arm 104 rotates about the first hinge arm 102, the ICoR of the second hinge arm 104 moves along the ICoR path. The ICoR path extends along an arcuate line through the first teeth 114 of the first end portion 106, generally corresponding to the first profile.

It will be appreciated that the first and second end portions of the present disclosure can vary together such that at any specific or particular rotational position of the lower or second hinge arm 104 relative to the upper or first hinge arm 102, the radius of the first end portion 106 or gear plus the radius of the second end portion 108 or gear is generally constant. It will be understood that the disclosed example is not limiting and that any relationship between any dimensions of portions of the hinge assembly 101 or an orthopedic device 100 of which the hinge assembly 101 is a part may be defined in any suitable manner.

The term "vertical" is defined as a direction generally along the tibial axis, while the term "horizontal" is defined as a direction generally perpendicular to the tibial axis in the sagittal plane. The terms vertical and horizontal can be relative to any corresponding limb and are not limited to the leg or in a fixed Cartesian space. Measurements provided herein are generally in reference to a traditional single point hinge, where the ICoR of a second or lower hinge arm 104 is fixed. There is no ICoR path because the ICoR does not move. There is no vertical or horizontal translation when the lower hinge arm 104 rotates relative to an upper hinge arm 102. Vertical shifting away from the knee center is defined as positive. Horizontal shifting towards the femoral frame is defined as positive.

Figure 4:
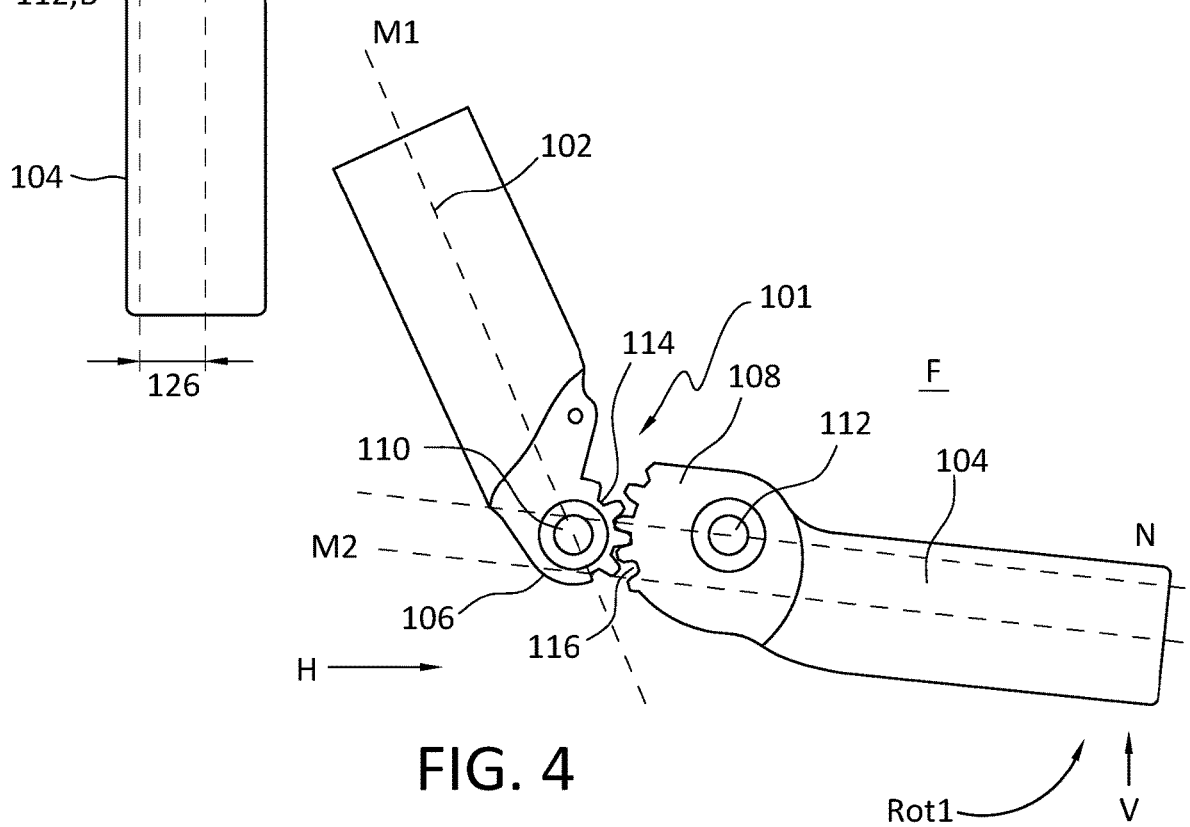
FIG. 4 is a schematic view of the hinge assembly of FIG. 2 in an idealized flexion configuration.

In FIG. 4, when the hinge assembly 101 moves from extension E toward flexion F, full flexion being at least 90°, the interaction between the teeth 114, 116 along with the first and second profiles of the first and second end portions 106, 108 shifts the second hinge arm 104 in both a vertical direction V and a horizontal direction H relative to the first hinge arm 102, producing a translational movement of the second hinge arm 102 in the hinge assembly 101. The second hinge arm 104 is shown shifting relative to the first hinge arm 102 in a positive vertical direction and a negative horizontal direction at about 90° of flexion.

As the user's knee K rotates back toward extension E or past a set flexion F angle, the contact or interaction between the teeth 114, 116 along with the profiles of the first and second end portions 106, 108 can move the second hinge arm 104 horizontally H and/or vertically V back toward its original position according to a desired path of rotation Rot1 corresponding, for example, to a particular joint of the body.

The pivoting movement of the second hinge arm 104 about an axis B over an opening 111 offset by the distance 126 according to the description of FIG. 1 relative to an axis A over an opening 109 of the first hinge arm 102 is defined or limited by the interaction between the first and second teeth 114, 116. The hinge assembly 101 is advantageously more robust and provides for greater control over the relative motion of the first and second hinge arms 102, 104 than prior art four-bar hinges, allowing for more versatile functional designs and reduced cost and complexity of use and manufacture. The axes A, B may be orthogonal to the longitudinal axes M1, M2, N.

The ICoR of the second hinge arm 104 is generally located at the point of contact between the first and second end portions 106, 108 along with the first teeth 114 on the first hinge arm 102. Because the ICoR is at or near the periphery of the second hinge arm 104, the translational movement of the second hinge arm 104 relative to the first hinge arm 102 can be limited for each degree of rotation. For instance, there may be a horizontal H shifting of the second hinge arm 104 during a specified range of flexion F or extension E. The desired shifting may vary from patient to patient, in that one patient may require a first amount of shifting whereas another patient having different anatomical proportions may require another amount of shifting. The orientation and profiles of the first and second end portions 106, 108 can be arranged according to the patient's individual needs accordingly.

Figure 5:
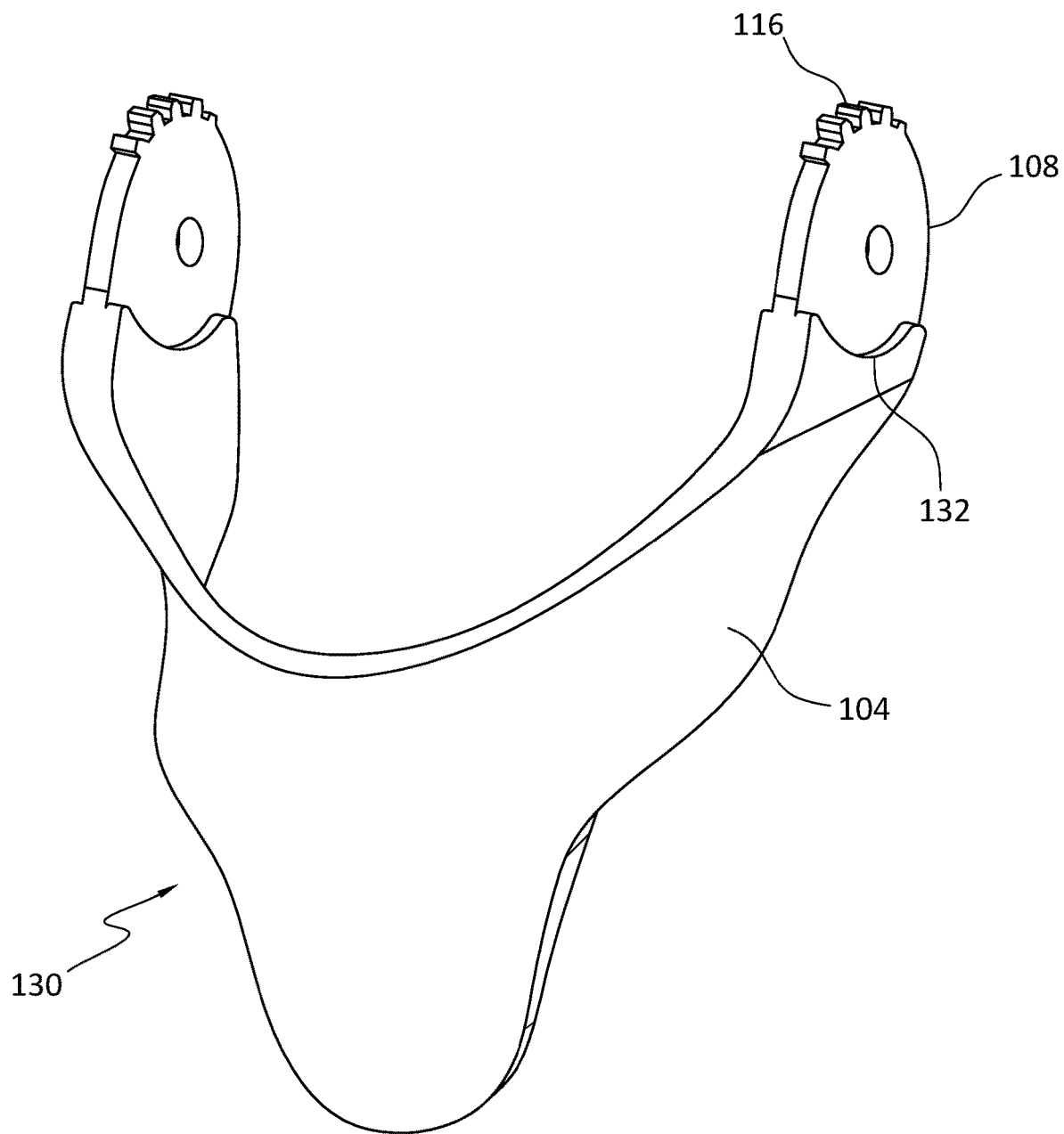
FIG. 5 is a perspective view of a lower frame in an orthopedic device forming the hinge arms with a body of the frame.

FIG. 5 illustrates how the second frame member 130 may be continuously formed with the second hinge arm 104, such that the second end portion 108 and second plurality of teeth 116 are all formed continuously from the same material and part. An accommodating feature, such as a recessed profile 132, may be provided to accommodate a hinge plate and movement of the hinge assembly 101.

Figure 6:
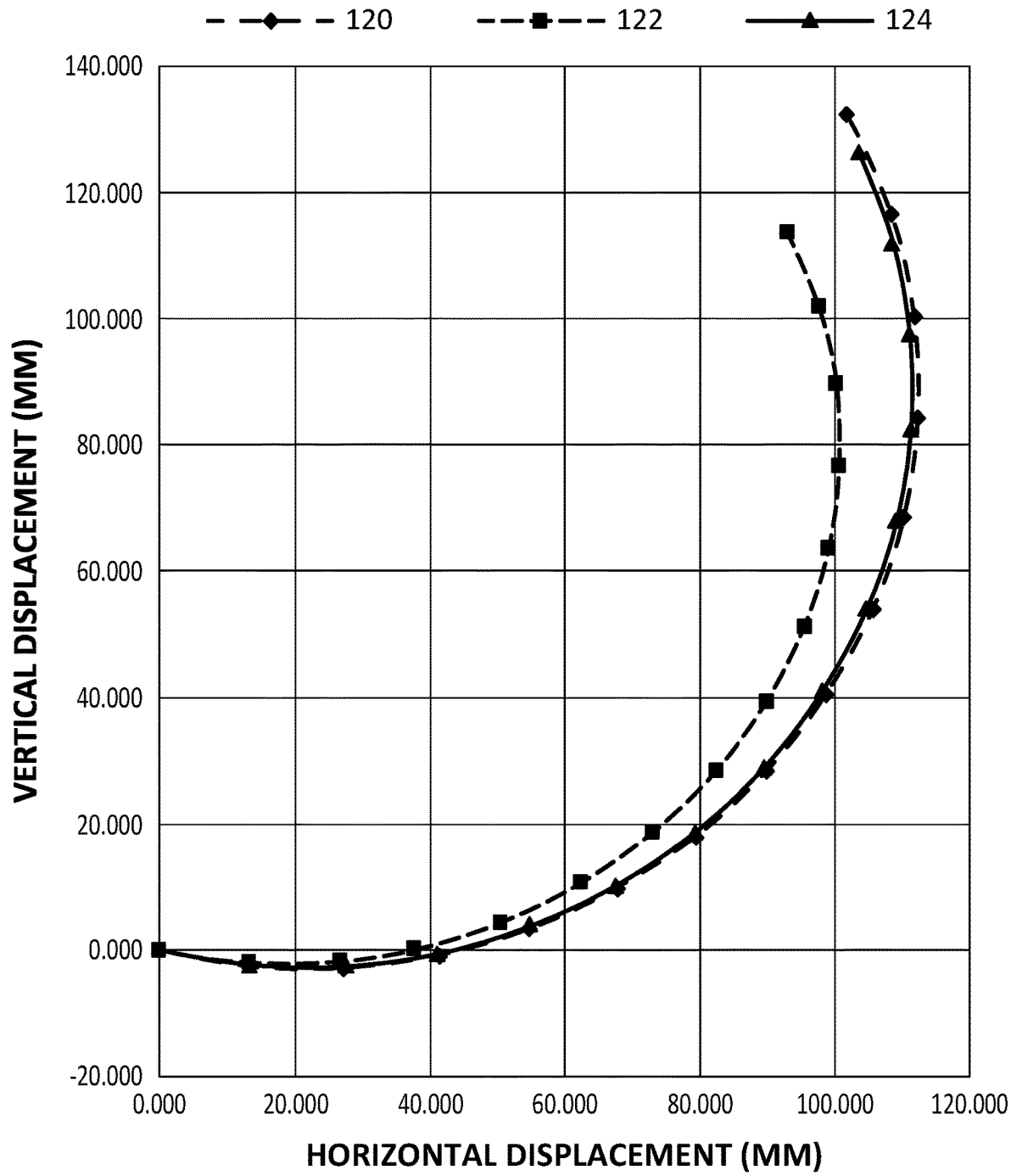
FIG. 6 is a graph depicting vertical versus horizontal displacement over different types of hinge assembly embodiments including the hinge assembly of the disclosure.

FIG. 6 shows a graph depicting the progression of vertical v. horizontal displacement during rotation over different types of hinge-assembly devices, including the hinge assembly of embodiments of the disclosure. A standard polycentric hinge 122 comprises hinge arms that follow a particular path of vertical v. horizontal displacement during rotation. A standard four-bar hinge 120 comprises hinge arms that follow a different path of vertical v. horizontal displacement, which path more closely approximates the natural motion of a knee joint but disadvantageously comprises a more complex and costly construction and is less robust than standard polycentric hinges.

A hinge assembly 124 according to embodiments of the disclosure likewise comprises hinge arms that follow a particular path during rotation. The vertical v. horizontal displacement path followed by the hinge assembly 124 embodiments advantageously track the path defined by a standard four-bar hinge 120 with greater accuracy than the standard polycentric hinge 122, and with improved cost, increased robustness, and reduced complexity relative to four-bar hinges 120. As seen, the path defined by the hinge assembly 124 of the disclosure and four-bar hinges 120 is virtually indistinguishable, resulting in a hinge movement, and consequently, a joint movement, that closely tracks the natural movement of a knee and with the structural advantages of the embodiments.

FIGS. 7A-7B and 8A-8B exemplify the hinge assembly 101 of FIG. 2 with an extension stop 150 and a flexion stop 180. A first or inner hinge cover 132 may be arranged for cooperating with the hinge assembly 101 according to principles of the disclosed embodiments, and may further provide a hinge plate 134 arranged for attaching to the first and second ends 106, 108 of the hinge assembly 101, and to a second or outer hinge cover 160. The first plate 134 defines a bias element 136 about which the extension stop 150 removably secures. The bias element 136 may define a guiding surface 140, a biasing surface 141, and a stabilizing extension 142, discussed in greater detail hereafter.

First and second pin extensions 144, 146 each form an elongate projection generally extending perpendicular from the first plate 134 and are adapted to extend through corresponding apertures or openings 109, 111 of the first and second hinge arms 102, 104. A base portion of the first and second pin extensions 144, 146 serve as bearing surfaces about which the first and second hinge arms 102, 104 may rotate. Distal end portions 145a, 145b of the pin extensions 144, 146 are adapted to extend through openings 168a, 168b formed by the second plate 162 of the second hinge cover 160 and project beyond the second plate 162 prior to coupling or welding of the first and second covers 132, 160.

An outer surface of the second plate 162 may form recesses 170 to enable coupling of the second cover 160 to the first cover 132 by serving as a location into which the distal end portions 145a, 145b may settle due to ultrasonic heat staking of the distal end portions 145a, 145b. As seen in FIG. 8A, the distal end portions 145a, 145b are illustrated prior to ultrasonic heat staking in that they extend beyond the second plate 162. FIG. 8B illustrates the distal end portions 145a, 145b after they have been ultrasonically heat staked in which they are essentially melted or shaped to be flush with the second plate 162 and settle in the recesses 170 to form a bond with the second plate 162, improving the aesthetics and the security of the attachment of the hinge assembly 101.

The second plate 162 likewise forms an opening 165 for accommodating a stabilizing extension 142, which projects beyond the second plate 162 before coupling of the first and second covers 132, 160, and ultrasonic heat staking, as illustrated in FIG. 8A. The stabilizing extension 142 interlocks with the second plate 162 to stabilize the first and second covers 132, 160 relative to one another. A recess 167 extends about the opening 165, and when ultrasonically heat staked, the stabilizing extension 142 fills the recess 167 to bond and extend flush against and with the second plate 162. Like the distal end portions 145a, 145b, the stabilizing extension 142 may be ultrasonically heat staked to be flush against and with a surface of the plate 162.

The extension stop 150 serves as an extension limit and may comprise an arm 152 extending from a base rotation portion 155 and a compression element 154 extending from the arm 152. The base rotation portion 155 may receive a fastener 138 extending from and/or removably securing to one of the first and second covers 132, 160. The fastener 138 may be a screw extending through a threaded aperture 139 defined by the second cover 160. The extension stop 150 forms an opening 156 at the base rotation portion 155 that receives the fastener 138. If it is desired to remove the extension stop 150, the fastener 138 may be removed, and the extension stop 150 can resiliently be removed from the bias element 136 by rotating the base rotation portion 155 away from the bias element 136.

In operation, the extension stop 150 may be arranged within or between the hinge plates 134, 162, and limit a degree of flexion or extension in a more comfortable and effective manner than existing devices. The compression element 154 may be formed from a resilient material such that, as rotation of the hinge arms 102, 104 brings the extension stop 150 into contact with a bias element 136, the compression element 154 is compressed between the biasing surface 141 and the stop-forming surface 153, the biasing surface 141 extending on an opposing side of a guiding surface 140. The compression element 154 may have a geometrical shape, such as an arcuate shape, to facilitate compression along with the material composition forming the compression element 154.

The act of compressing the compression element 154 in this manner provides a soft bump or a damping effect as the limit on extension is reached, enhancing comfort for a user over a sudden, hard stop as in existing extension limits. The arm 152 may be formed from a less resilient material than the compression element 154; alternatively, a substantial entirety of the extension stop 150 may be formed from a resilient material. The extension stop 150 further protects the user and components of the hinge assembly from damage from hard impacts between hinge arms and conventional flexion/extension stops.

The extension stop 150 may be engaged around a guiding surface 140 of the bias element 136 at which flexion/extension is to be limited, and selectively removed when no limit is needed. The extension stop 150 may be configured to correspond to a configuration of the bias element 136, so the arm 152 may define a profile complementary to a profile of the guiding surface 140, thereby ensuring intuitive and reliable engagement.

The base portion 155 has a corresponding profile to a base of the bias element 136 so as to fittingly secure therewith, just as the arm 152 has a corresponding profile to the guiding surface 140 whereby the compression element 154 resiliently biases against the biasing surface 141. For installing the extension stop 150, the compression element 154, which forms an arch with the arm 152, is placed over a top of the bias element 136, and the base portion 155 is rotated to engage the base of the bias element 136 to snap-fit with the bias element 136 as the compression element 154 counteracts the base portion 155.

For removal of the extension stop 150, the base portion 155 may be rotated away from the base of the bias element 136, and the compression element 154 is elevated above the bias element 136 and removed. In either installation or removal, it is preferable that the hinge assembly 101 is in a flexion position to offer sufficient clearance for moving the extension stop 150 relative to the bias element 136.

The compression element 154 may define an arcuate profile 157 and biases against a biasing surface 141 of the bias element 136 or may have an end portion bias against the biasing surface 141, with a gap 151 between the compression element 154 and the biasing surface 141 except for the end portion. As the hinge 101 rotates into extension, the gap 151 between the biasing surface 141 and the compression element 154 reduces; the compression element 154 increasingly provides resistance into extension. The end portion may slide along the biasing surface 141 as the hinge 101 goes into extension to accommodate flattening of the compression element 154 as it is increasingly wedged between the biasing surface 141 and a stop-forming surface 153 of the first end portion 128.

FIG. 8A shows the hinge assembly 101 generally in extension, whereas FIG. 8B shows the hinge in flexion. FIG. 8A shows the extension stop 150 cooperating with the first frame member 128 and the first end portion 106, engaging both to nestle and compress therebetween and prevent further extension of the hinge 101. FIG. 8B shows how the extension stop 150 is effectively relieved of compression while the compression element 154 may slidably engage the stop-forming surface 153 of the first end portion 106.

Multiple extension stops 150 may be engaged at different points around the hinge 101 and are not limited in shape, configuration, number, properties, or otherwise to the depicted embodiments. The extension stop 150 may be arranged for removal from the hinge assembly 101 in any suitable manner, including by being removed from between the hinge plates 134, 162 in a lateral manner, or by being inserted/removed from the hinge assembly 101 by removing one of the hinge plates 134, 162 and lifting the extension stop 150 out of the hinge assembly. Multiple extension stops 150 having different properties may be provided so the damping or other properties may be closely tailored to a user or patient's individual needs.

A flexion stop 180 may also or alternatively be provided on an opposite side of the hinge assembly 101. The flexion stop 180 may be selected from many flexion angles to stop rotation of the hinge assembly 101 at such selected angle. The flexion stop 180 is removably secured to the hinge assembly 101 and has a profile arranged for cooperating with the first and second end portions 106, 108 to arrest rotation of the of the hinge assembly 101 at the prescribed flexion angle.

Figure 7A:
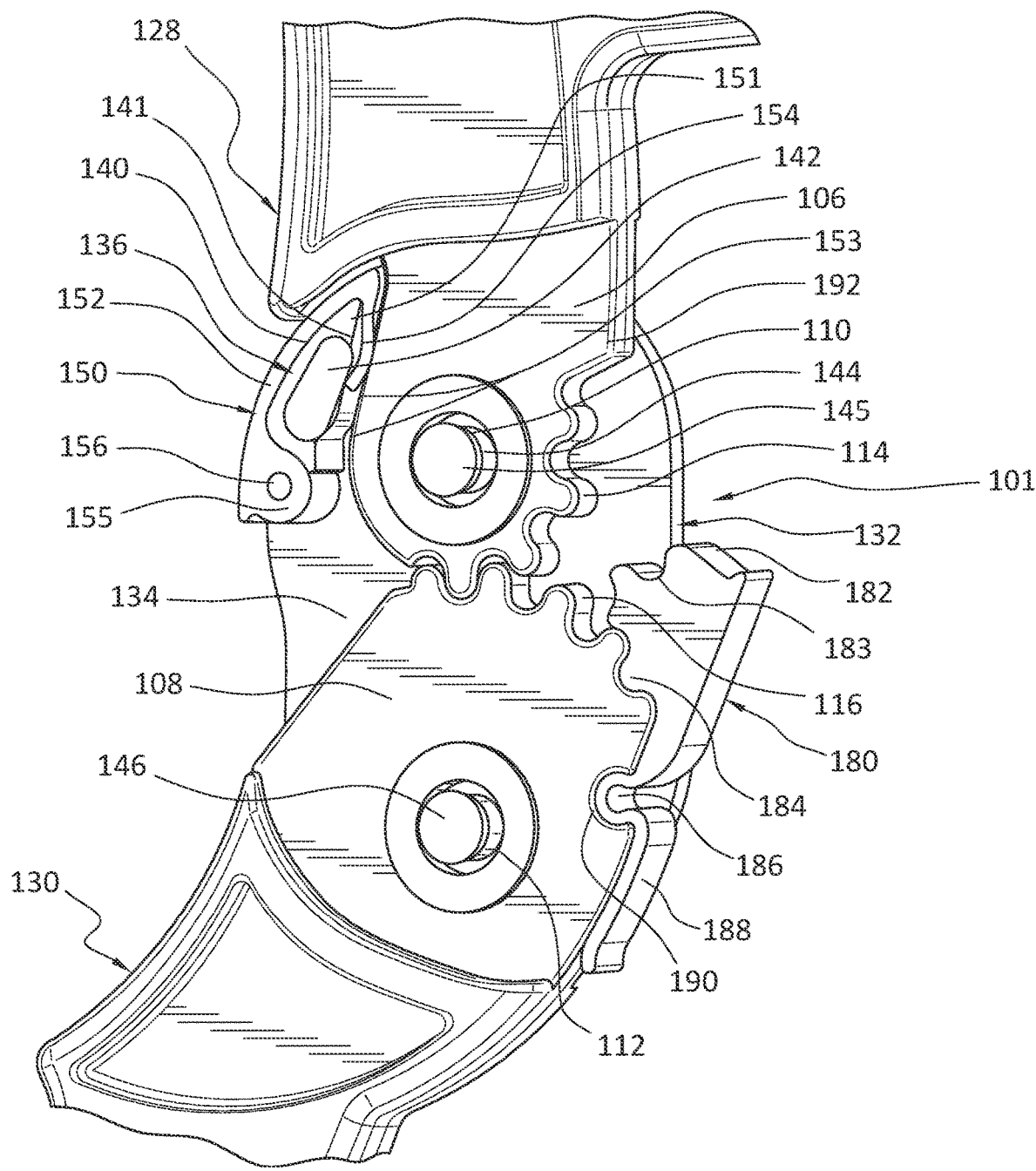
FIG. 7A is a perspective view of the hinge assembly in FIG. 2 including extension and flexion stops with the hinge assembly in extension and an outer plate removed.
Figure 7B:
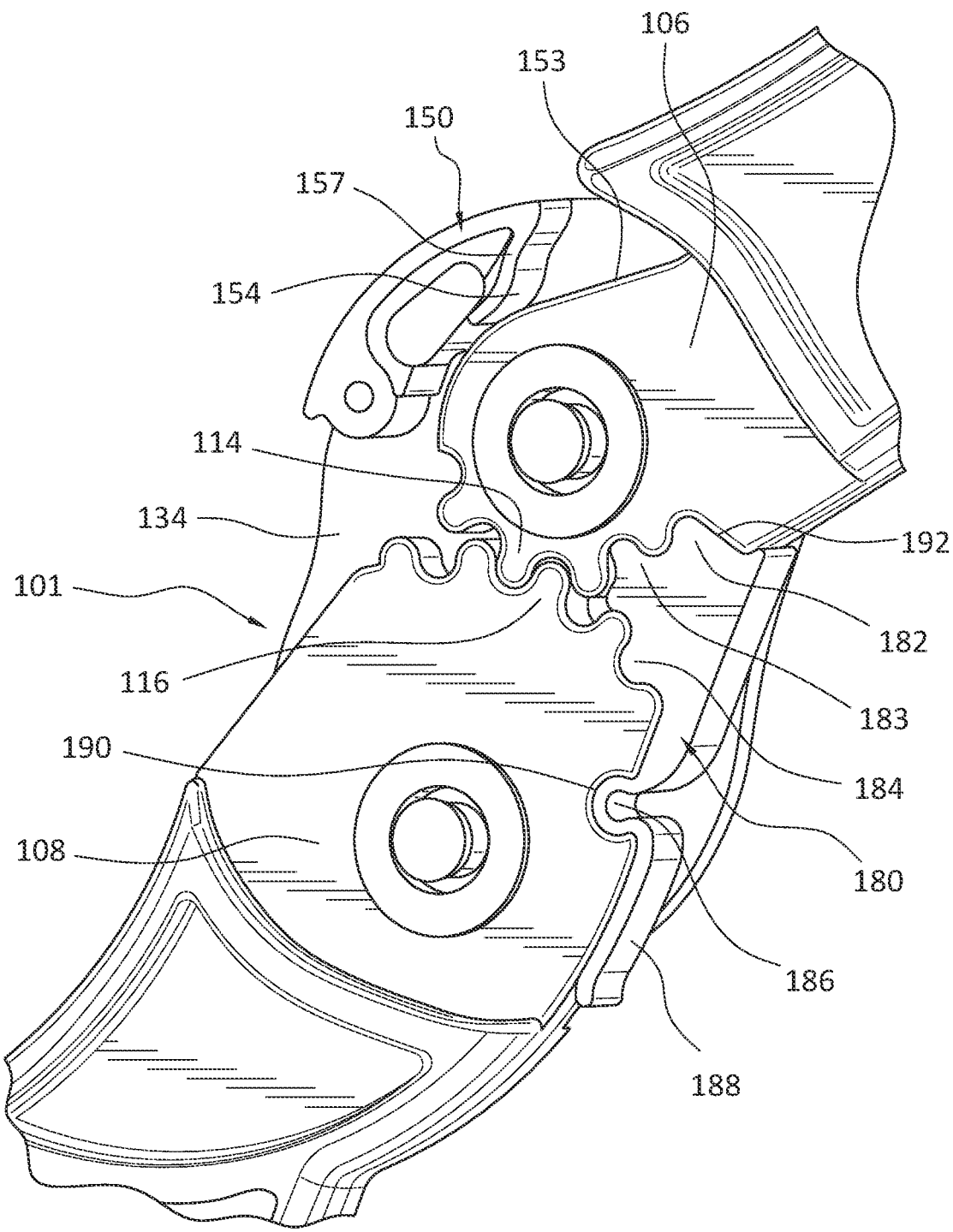
FIG. 7B is a perspective view of the hinge assembly in FIG. 7A with the hinge assembly in flexion.

Referring to FIG. 7B showing the flexion stop 180 preventing further rotation at 60°, the flexion stop 180 has a top portion 182 engaging a stop surface 192 of the first end portion 106. The flexion stop 180 forms a first stop portion 183 engageable with the first teeth 114 and a second stop portion 184 engageable with the second teeth 116, which serve as a wedge to prevent further rotation.

As the flexion stop 180 is removably securable, in the depicted embodiment, the flexion stop 180 is retained by the second end portion 108, particularly from an outside perspective. The outside perspective enables a user to snap fit a snap element 186 into a receptacle 190 formed along a surface of the second end portion 108 accessible from outside of the first and second covers 132, 160. A prong 188 extends from the flexion stop 180 and generally beyond the snap element 186 to enable a user to articulate the flexion stop 180 into and from the receptacle 190. The prong 188 provides stability to the flexion stop 180 when retained by second end portion 108 as it extends along the periphery of the second end portion 108, but also serves as a leverage arm for disengaging the snap element 186 from the receptacle 190.

By providing a hinge assembly for an orthopedic device according to embodiments of the disclosure, the problem of hinges insufficiently tracking the natural anatomical movement of a joint is addressed, as is the problem of existing solutions providing costly, complex, and non-robust four-bar hinges to provide accurate tracking of natural movement. The hinge assembly of the disclosure advantageously provides a cost-effective, robust, and intuitive solution that closely approximates natural movement. Further, by providing an improved flexion/extension stop, a user is provided with a hinge assembly having greater comfort, interchangeability, and durability than existing flexion/extension stops.

While the disclosure discusses embodiments for the knee, hinge assembly embodiments of the disclosure may be used with other limbs, joints and anatomical portions including the torso, shoulder, elbow, wrist/hand, hip, knee, and foot/ankle. Embodiments of the hinge assembly may be used in other orthopedic, prosthetic, medical, and other devices, and are not limited to the embodiments shown.

Figure 9A:
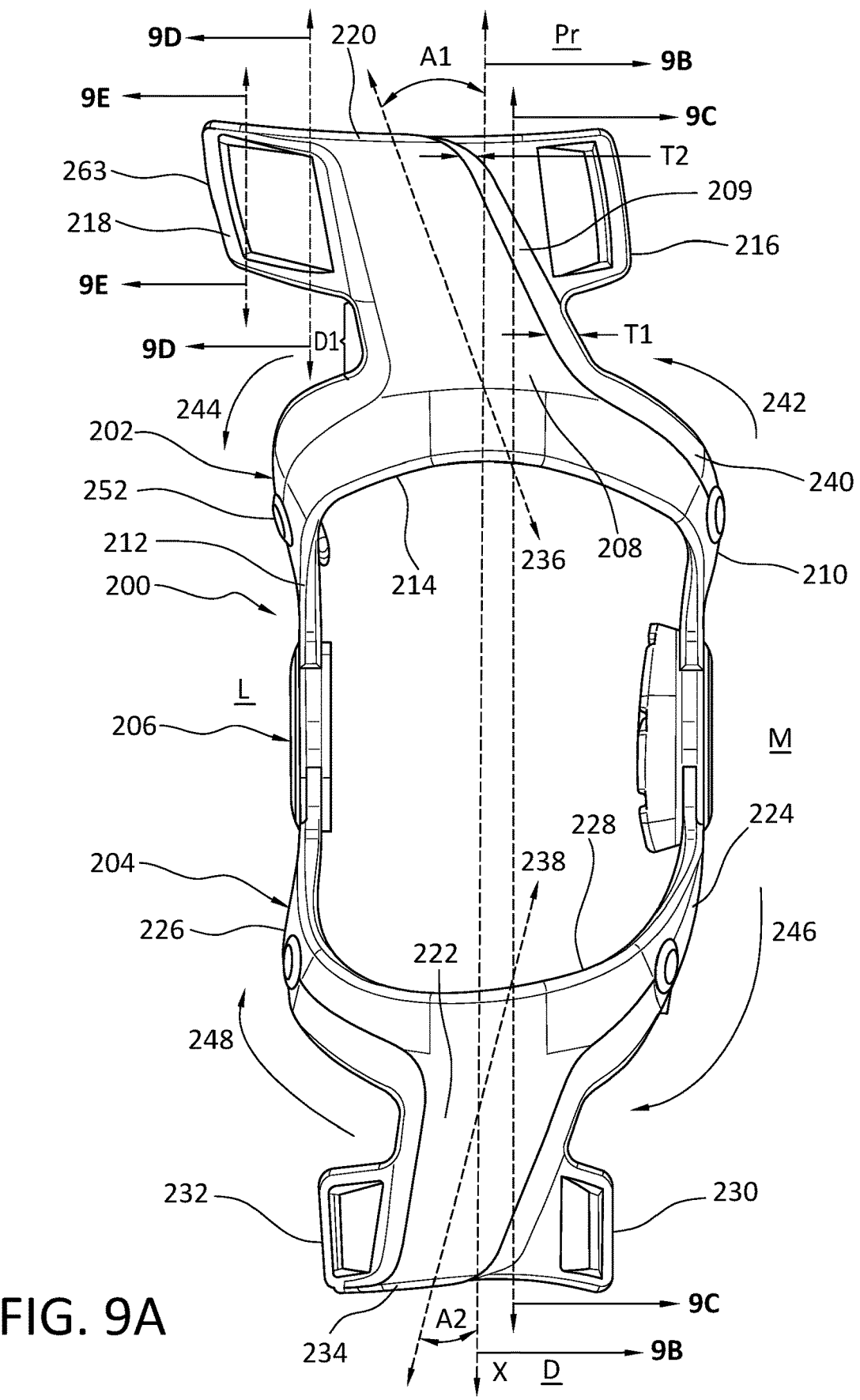
FIG. 9A is an elevational view of an orthopedic device having the hinge assembly according to the disclosure.

FIG. 9A illustrates an orthopedic device in a knee brace 200 that may include the aforementioned hinge assembly embodiments. The knee brace 200 includes a first or upper frame component 202 adapted to secure about a user's upper leg and correspond to a femur. The first frame component 202 is connected to a second or lower frame component 204 adapted to secure about a user's lower leg and correspond to a tibia. The first and second frame components 202, 204 are connected to one another by a hinge assembly 206, preferably formed integrally from at least part of the first and second end portions of the first and second frame components 202, 204.

The knee brace 200 is arranged to be used for increased anterior-posterior and medial-lateral stability around the knee, including anterior-cruciate ligament, medial-cruciate ligament and posterior cruciate ligament, rotary and combined instabilities. Particularly, the first frame component 202 is arranged relative to the second frame component 204 to create three main points of contact: (1) lateral tibia; (2) medial condyle; and (3) lateral thigh. The three main points of contact prevent side impact blows to protect the aforementioned ligaments of the knee.

The first frame component 202 defines a first mast 208 generally depending centrally from a first central segment 214 extending between a first medial strut 210 and a first lateral strut 212. The second frame component 204 likewise has a second mast 222 generally depending centrally from a second central segment 228 extending between a second medial strut 224 and a second lateral strut 226. From FIG. 9A, the first and second frame components 202, 204 laterally sway from a central vertical axis X-X. The lateral sway is formed at least in part to accommodate a standard Q-angle to provide near-universal fit, thereby providing a knee brace arranged to accommodate near universality in sizing for users.

The Q-angle is measured by extending a line through the center of the patella to the anterior superior iliac spine and another line from the tibial tubercle through the center of the patella. The direction and magnitude of force produced by the quadriceps muscle has great influence on patellofemoral joint biomechanics. The line of force exerted by the quadriceps is lateral to the joint line, mainly due to the large cross-sectional area and force potential of the vastus lateralis. Since there exists an association between patellofemoral pathology and excessive lateral tracking of the patella, assessing the overall lateral line of pull of the quadriceps relative to the patella is a meaningful clinical measure.

The lateral sway of the first frame component 202 is evidenced by the sway of arrows 242, 244, and the second frame component 204 is evidenced by the sway of arrows 246, 248, relative to the vertical axis X-X. The first and second masts 208, 228 are angled relative to the vertical axis X-X to accommodate the Q-angle, as evidenced by arrows 236, 238. For example, the first and second masts 208, 228 may be arranged at angle A1, A2 6°±2° from the vertical axis X-X, and more specifically 3°±1.0°, to provide for the near-universal fit.

As the knee brace 200 may be arranged as an off-the-shelf brace, the lateral sway and Q-angle arrangement of the first and second frame components 202, 204 are provided to create "brace to bone" contact. While in a custom brace a clinician can exaggerate the lower frame profile to best capture an individual's tibia/tibialis, it is more difficult to do with an off-the-shelf knee brace, particularly if an individual does not fall within parameters of a knee brace profile (i.e., more varus or valgus tilt). Such poor-fitting may cause undesirable tibial pressure or other pressure points along with the masts 208, 222.

In the arrangement of the knee brace of FIG. 9A, the criticality of the lateral sway and accommodation of the Q-angle in a preferred range, but not limitative, of 3°±1.0° range, softens the profile of the knee brace to accommodate a wider range of individuals. A standard Q-angle of 6°±2° may be found in conventional off-the-shelf prior art knee braces, but while such a Q-angle may be a median angle for a wide field of users, the prior art knee braces are found to mismatch with many users, particularly once considered in combination with hinges, liners and throughout gait (extension to flexion), which may vary the fit even further so on the individual. Such mismatch makes many off-the-shelf knee braces less desirable for use.

While a Q-angle range of 6°±2° may be typical in conventional off-the-shelf knee braces to match a median Q-angle of users, it has unexpectedly been found that a smaller Q-angle of 3°±1.0° can accommodate more users of a knee brace, mainly when other features of the knee brace are considered. The profile of the knee brace 200 is provided in combination with liners, as discussed in connection with condyle pads of FIGS. 11A-11F and liners of FIGS. 12A-12C, that provide sufficient capture and tunability of the knee brace to a greater field of users, while the rigid or semi-rigid first and second frame components have a softer Q-angle configuration over conventional off-the-shelf knee braces.

Figure 9B:
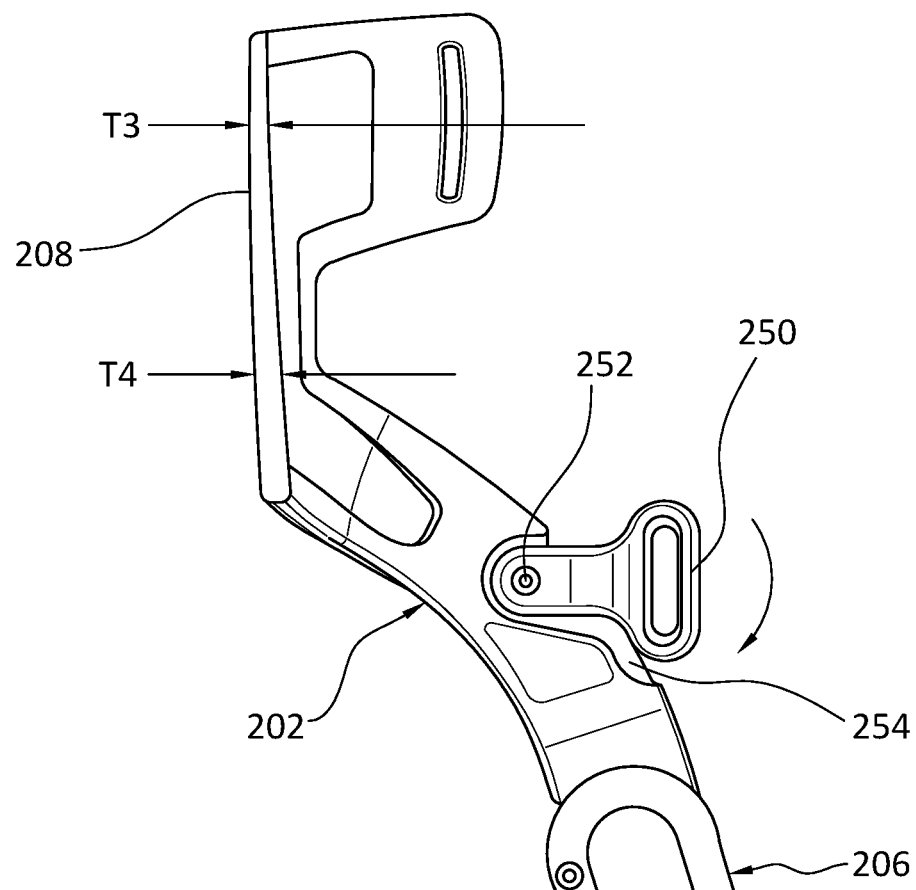
FIG. 9B is a cross-sectional view of the orthopedic device of FIG. 9A taken along line 9B-9B.

FIG. 9B shows how the first and second frame components 202, 204, may have recesses and other features for accommodating accessories, as in the D-rings 250. The first and second frame components 202, 204 have a contoured recess 254 accounting for rotational movement relative to the first and second frame components 202, 204. The contoured recess 254 is preferably configured to limit the extent by which the D-rings 250 rotate relative to the first and second frame components 202, 204. The D-rings 250 may be secured to the first and second frame components 202, 204, by a fastener 252.

Additionally, the contoured recess 254 is configured to eliminate pressure points on a patient or user's skin. By providing the contoured recess 254, the D-rings 250 may be supported and exert forces against a surface of the orthopedic device 200 rather than exerting all of the forces applied by the D-rings 250 directly onto a user or patient's skin.

Referring to the first mast 208, medial and lateral arms 216, 218 extend from the first mast 208 a distance D1 from the first central segment 214. Because of the first and second masts 208, 222, the first and second central segments 214, 228 are more proximate to the knee and create a frame configuration the limits that lengths of the first and second medial and lateral segments 224, 226, 210, 212, thereby maintaining the first and second central segments 214, 228 closer to the knee. Such low profile of the first and second frame components 202, 204 about the knee is particularly advantageous when the knee brace 200 is worn during physical activities as the first and second frame components 202, 204, aside from the first and second masts 208, 222, extend minimally along the user's leg, while providing sufficient support and security to the user's leg.

As shown, the masts 208, 222 may be rigid and may "lean into" the lateral arms 216, 218, 230, 232, as depicted in FIG. 9A. By leaning into the lateral arms 216, 218, 230, 232, a transition of rigidity to relative flexibility may be formed, and not significantly apply pressure points on the flesh and bone of the user. Such more natural transition from the rigid masts 208, 222 to the lateral arms 216, 218, 230, 232 may likewise improve anti-migration properties of the knee brace 200 as it is more ergonomically contoured universally over prior art knee braces, with some give allowing for a better fit as the lateral arms 216, 218, 230, 232 transition away from the rigid masts 208, 222.

The first mast 208 is preferably rigid, although, as shown in FIG. 9B, the first mast 208 has a tapered thickness, such that the thickness T4 is greater at a distal end compared to a proximal end at thickness T3. The thickness T4 is greater than the thickness T3 in part as it extends from the first central segment 214 and enables the insertion of features, such as supporting fasteners for a patella cup and other accessories. The greater thickness T4 blends with the first central segment 214 and is integrally formed therewith, and increases the central mass rigidity of the knee brace 200. The second mast 222 is arranged similarly as the first mast 208 regarding the tapering of thickness T5 at the second central segment to the distal end having thickness T6.

Both the first and second masts 208, 222 have a crescent-shaped relief edge 220, 234 whereat the thickness of the first and second masts 208, 222 is most minimal, as depicted in FIG. 9B. The crescent-shaped relief edge reduces possible pressure the first and second masts 208, 222 may apply to the femur and tibia, respectively, and provide an improved fit over conventional orthopedic devices having a more pointed configuration.

The first mast 208 has first medial and lateral arms 216, 218, and the second mast 222 has second medial and lateral arms 230, 232. The lateral arms 218, 230 provide increased support in comparison to flexible subshells in prior art braces and are integrally formed from the first and second masts 208, 222, which are, in turn integrally formed from the first and second central segments 214, 228. The lateral arms 218, 232 are arranged to resist a load exerted thereon, and are arranged to extend or rotate less than a quarter of a circumference of a user's leg, such as less than 60° from the vertical axis X-X, and more particularly less than 45° from the vertical axis X-X.

Figure 9C:
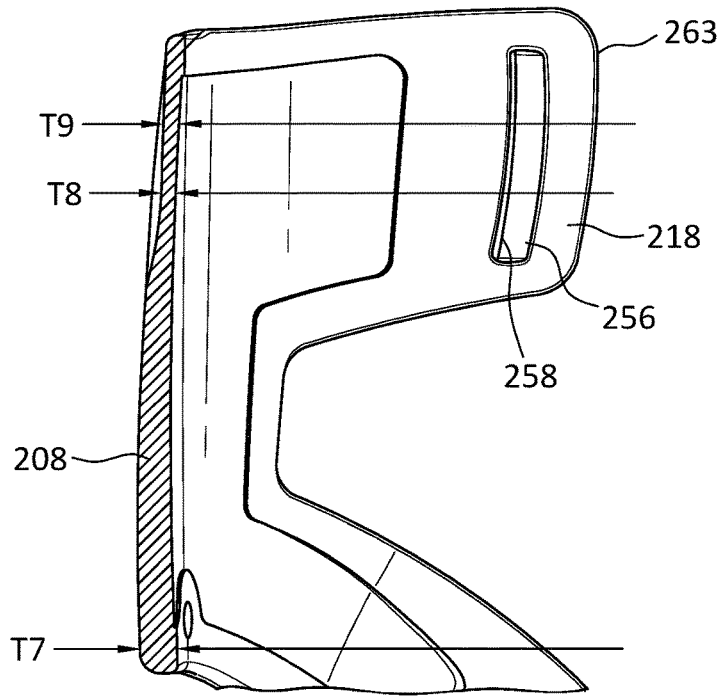
FIG. 9C is a cross-sectional view of the orthopedic device of FIG. 9A taken along line 9C-9C.

In transitioning from the first mast 208, FIG. 9C illustrates how the thickness of the first mast 208 may have a variable taper extending from a distal end at thickness T7 to the proximal end at thickness T9 in a generally vertical direction. The thickness may also vary generally horizontally at thickness T8 along transition regions 209 of the first mast 208. The thickness of the first mast 208 relative to the first medial and lateral arms 216, 218, may likewise vary from distal to proximal directions D, Pr along the vertical axis X-X, to provide a gentle transition in rigidity to the medial and lateral arms 216, 218.

Figure 9F:
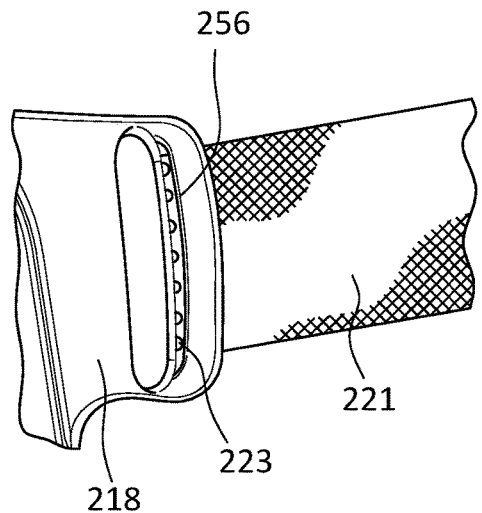
FIG. 9F is an embodiment of a strap attachment in the orthopedic device of FIG. 9A.
Figure 9D:
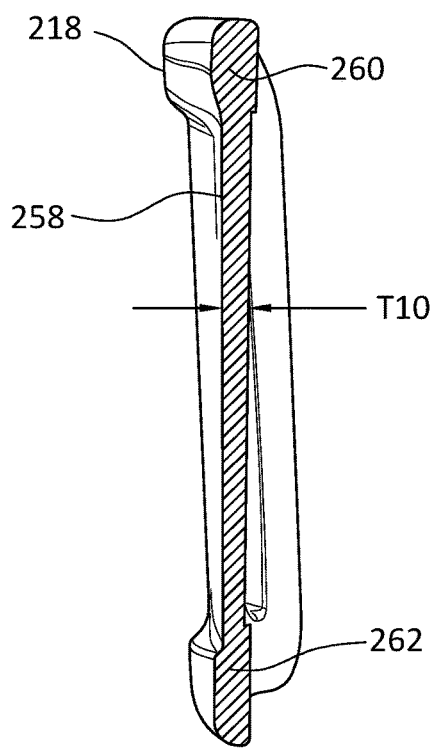
FIG. 9D is a cross-sectional view of the orthopedic device of FIG. 9A taken along line 9D-9D.
Figure 9E:
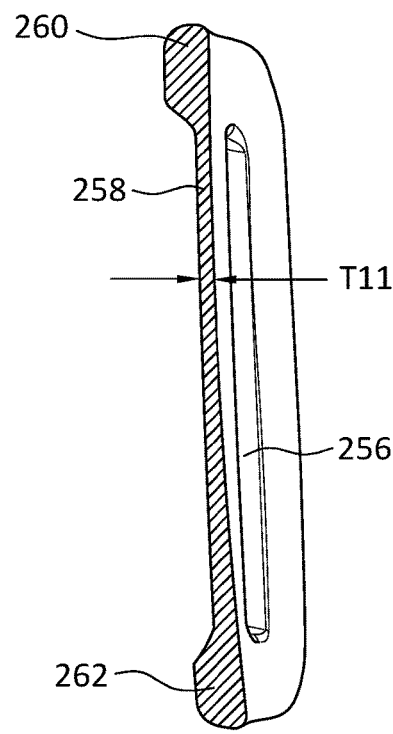
FIG. 9E is a cross-sectional view of the orthopedic device of FIG. 9A taken along line 9E-9E.

As shown in FIGS. 9D and 9E, the lateral arms 218, 222, exemplified by the first lateral arm 218, has tapered thickness T10, T11, as the lateral arm 218 extends away from the first mast 208. Compared to the first mast 208, the lateral arm 218 becomes increasingly thinner as it extends away from the first mast 208, and is consequently more flexible than the first mast 208. The first mast 208 is arranged to be rigid or semi-rigid, preferably very rigid, by the lateral arm 218 becomes relatively progressively more flexible to provide more flexibility or give to accommodate a wide spectrum of users while providing sufficient support in loading scenarios of the knee brace 200. The tapered thickness achieves a fine balance of rigidity for support, and flexibility for improved fit, perception of fit, and comfort.

To achieve the improved fit and comfort while achieving a balance of rigidity and flexibility, the lateral arm 218 has thickened first or upper and second or lower edge portions 260, 262, while the center portion 258 between such first and second edge portions 260, 262 remains thinner. The first and second edge portions 260, 262 in combination with an end edge portion 263 may form the center portion 258 as being recessed relative to the edge portions 260, 262, 263, with the edge portions 260, 262, 263 providing the superstructure to maintain sufficient rigidity.

The center portion 258, being recessed, may enable some give when a strap 221 is secured therewith, as depicted in FIG. 9F. In the variation of FIG. 9F, the strap 221 may be anchored to the lateral arm 218 by a retainer 223, which is sized larger than a slot 256 having a periphery 258, formed by the lateral arm 218. The strap 221 extends from the retainer 223 and through the slot 256.

To achieve the desired characteristics of a balance of sufficient rigidity and flexibility, as well as being lightweight on a mass scale suitable for off-the-shelf braces, the first and second frame components 202, 204 are preferably constructed from long fiber reinforced thermoplastic materials. By being "long fiber," the fibers are defined as individual reinforcing fibers having a uniform length and in parallel alignment with each other. For example, the individual reinforcing fibers are aligned regarding each other and are generally exactly as long as a pellet using in the injection molding process. In comparison, short fiber reinforced thermoplastic materials contain reinforcing fibers of various short lengths randomly oriented in the resin pellet.

In the preferred embodiments of the first and second frame components 202, 204, they are formed from long fiber individual reinforcing fibers, which enable the first and second frame components 202, 204 to have superior and predictable mechanical performance as compared to short fiber reinforced thermoplastic materials. An exemplary long fiber reinforced thermoplastic material is provided by Plasticomp LLC of Winona, MN, under the product name Complēt LCF40-PA66 M T 1014 NAT. The product uses a thermoplastic resin of Nylon 66, and the long fiber is carbon, with a fiber content of 40%.

From the long fiber individual reinforcing fibers and due to the injection molding process of the thermoplastic resin, the material properties of the first and second frame components 202, 204 have improved material properties, such as tensile and impact strength, weight and dimensional stability, and with discrete zones of relative enhanced rigidity (i.e., struts, central segment, and masts) relative to other zones (as in the medial and lateral arms). The long fiber reinforced thermoplastic material forming the first and second frame components forms an improved bearing surface, which enables the hinge arms themselves to be formed from the first and second frame components, as opposed to using metal inserts commonly found in knee braces constructed from thermoset resin impregnated carbon fiber. As is well understood in the art of carbon fiber processing, and more particularly in prosthetics and orthopedics, such thermoset resin impregnated carbon knee braces are typically made by hand-laid processing, as opposed to the injection-molded design of the orthopedic device.

Regarding weight, the high strength-to-weight ratio of the long fiber-reinforced thermoplastic material reduces the weight of the knee brace over conventional knee braces formed from metal and/or carbon fiber composite using a thermoset polymer. Over a prior art knee brace discussed in U.S. Pat. No. 7,749,183, granted on Jul. 6, 2010, and incorporated herein by reference, which has a weight of 700 grams and is formed from carbon fiber with a thermoset resin and uses metal inserts for the hinge assembly, the knee brace of FIG. 9A of comparative size has a weight of 430 grams, due to the long fiber reinforced thermoplastic material construction of the first and second frame components 202, 204.

As the first and second frame components 202, 204 are injection molded to shape, minimal post-mold finish work is necessary. For example, the first and second frame components 202, 204 are molded into a definitive shape, so that preferably no sanding, bonding, or paint is necessarily required. By molding the shapes from an initial definitive mold, there is a high degree of freedom in initially shaping the first and second frame components, with the aforementioned thickness variations definitively formed when molded into shape from the long fiber-reinforced thermoplastic material.

Figures 10C, 10D, 10E:
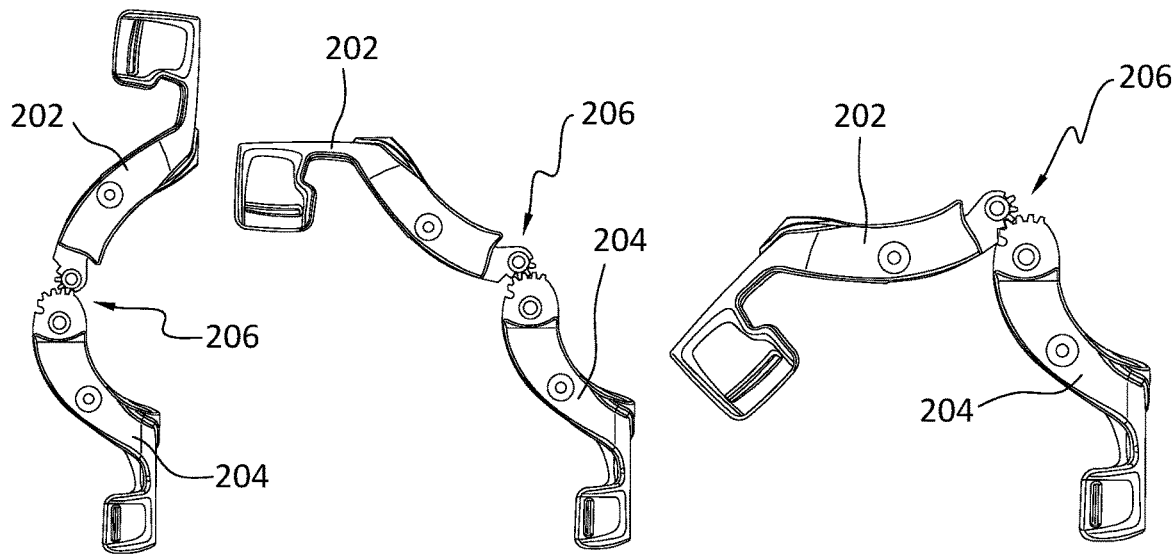
FIGS. 10C-10E are schematic elevational views of the orthopedic device of FIG. 9A over a flexion cycle.

FIGS. 10A-10F exemplify how the motion tracking of the hinge assembly 207 compares to similar hinge assembly designs. FIG. 10A shows how the hinge assembly 207 including first and second hinge arms 264, 266 are formed integrally as part of the first and second frame components 202, 204 of the same material and simultaneously when the first and second frame components 202, 204 are injection molded. The first and second hinge arms 264, 266 are preferably continuous with the medial and lateral struts, without interruption, being of the same material and structure, so the material forming the first and second hinge arms 264, 266 blends with the same material forming the medial and lateral struts. Surface reliefs 268, 270 may be formed to accommodate hinge plates (as discussed above) and reduce a thickness of the first and second hinge arms 264, 266 relative to the medial and lateral struts of the first and second frame components.

FIG. 10A shows how the hinge assembly 206 is arranged at angle A3, generally corresponding to a hinge orientation wherein the hinge orientation is 15° relative to a vertical plane 269. FIG. 10B shows how the hinge assembly 207 is oriented at 25° relative to the vertical plane 269. In comparing hinge assembly 206 to hinge assembly 207, the first and second lateral struts 212, 226 of the first and second frame components 202, 204 are more consistently shaped similarly relative to one another than in the first and second frame components 202A, 204A relative to the first and second lateral struts 212A, 226A. Such arrangement allows for better capture of the first and second frame components 202, 204 to a universal fit of a leg, relative to the first and second frame components 202A, 204A, without significantly diverging from the desired tracking motion. The arrangement of the first and second frame components without sacrificing the tracking motion also allows for improved lateral support by the shape of the first and second frame components in FIG. 10A and improved brace performance.

FIGS. 10C-10E illustrate the general motion of the first frame component 202 relative to the second frame component 204 of the hinge assembly 206, whereas FIG. 10C illustrates extension, FIG. 10D illustrates flexion at 90° and FIG. 10E illustrates flexion at about 120°. The hinge assembly 206, operates as the hinge assembly of foregoing embodiments.

Figure 10F:
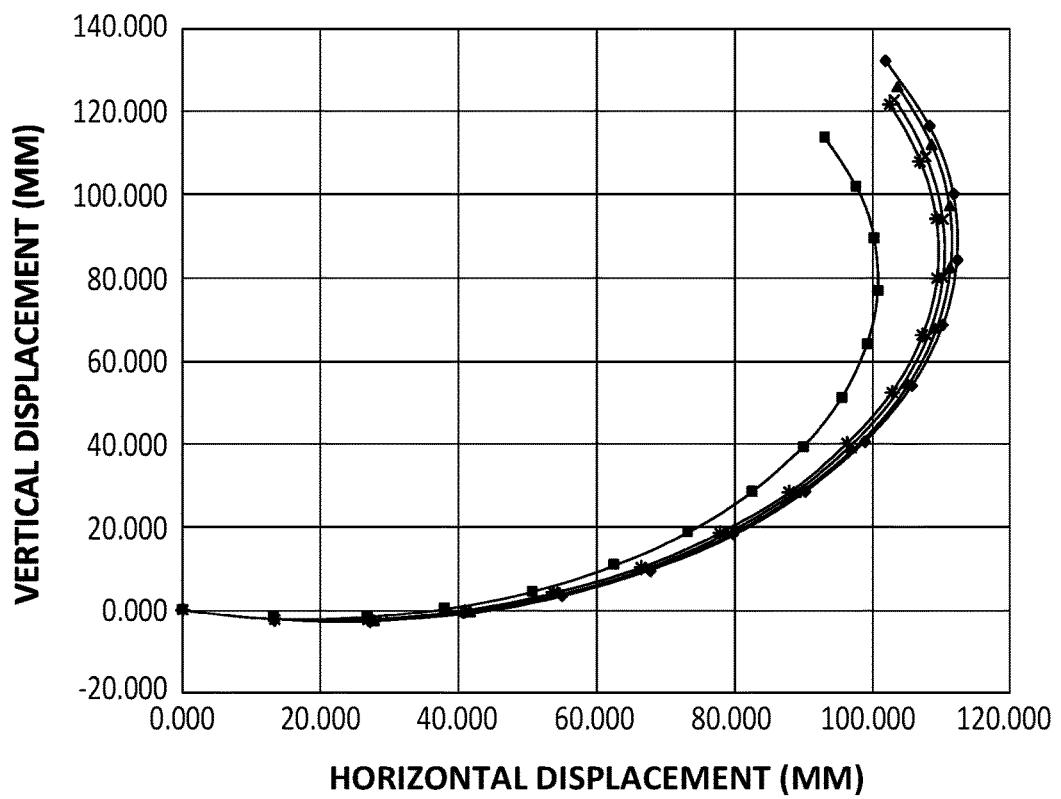
FIG. 10F is a graph depicting hinge type displacement of vertical over horizontal.

FIG. 10F exemplifies how the hinge assembly of FIG. 10A has hinge motion tracking compared to a standard four-bar hinge, as discussed in U.S. Pat. No. 8,979,782, granted on Mar. 17, 2015, and U.S. Pat. No. 4,856,501, granted Aug. 15, 1989, each of which is incorporated by reference, and a polycentric hinge, as discussed in U.S. Pat. No. 10,588,770, granted Mar. 17, 2020, and incorporated by reference. Different hinge arm angles are compared, with the 15° exemplifying little difference in hinge arm tracking compared to a standard four-bar hinge and 25° and 17° hinges while possessing improved frame leg capture due to the shape of the 15° hinge assembly in the knee brace of FIG. 10A.

Figures 11A, 11B, 11C:
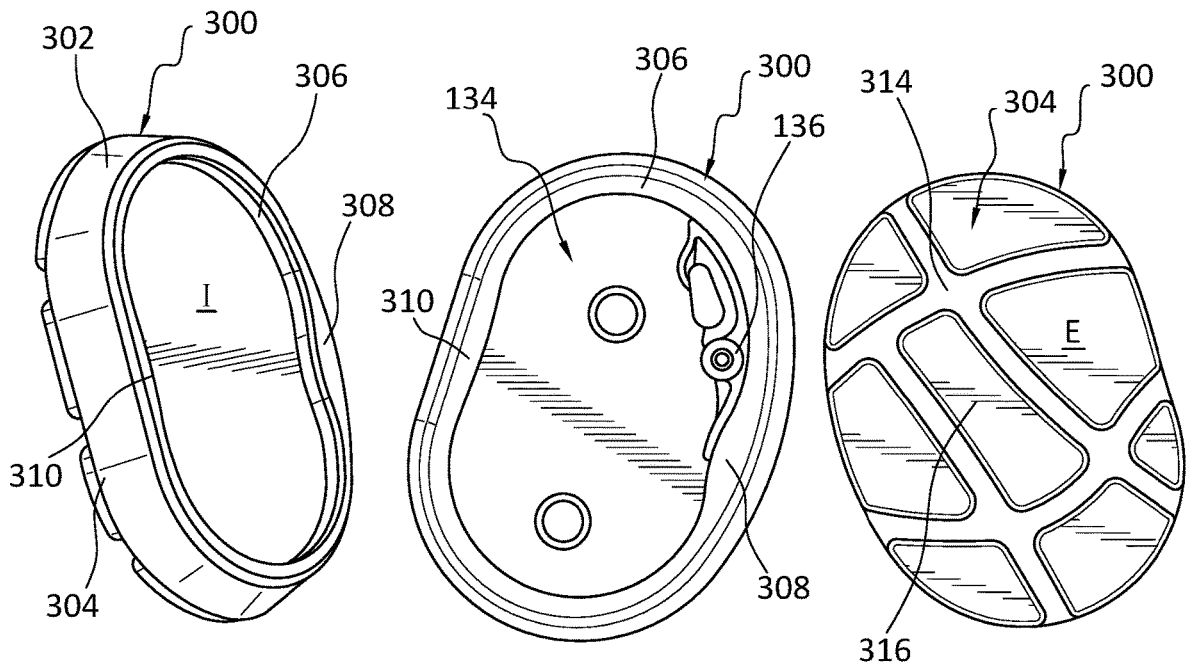
FIG. 11A is a perspective view of a condyle pad in the embodiment of FIG. 9A.
FIG. 11B is a schematic view of the condyle pad of FIG. 11A secured to a hinge plate of FIG. 9A.
FIG. 11C is an elevational view of the condyle pad of FIG. 11A showing an exterior side.

FIGS. 11A-11F illustrate a condyle pad 300 anatomically configured to account for the Q-angle and lateral shift and offers improved capture and tunability for comfort and usability. FIG. 11A shows the condyle pad 300 as having a body 302, a tread pattern 304 extending from the body 302 along an exterior side (the side facing the user), and a recess 306 along the interior side (the side facing the hinge assembly). Concerning the recess 306, it is generally shaped to a corresponding shape of the hinge plate 134, including surface reliefs 308, 310 adapted for grasping the hinge plate 134, and corresponding to the contours of the hinge plate 134 and bias element 136. The depth of the hinge plate 134 is proximate to a thickness of the hinge plate 134. The condyle pad 300 preferably is formed from EVA (ethylene-vinyl acetate), which provides superior softness and flexibility over foam-based condyle pads. Because of the EVA construction, the condyle pad 300 is resilient to fit over the hinge plate 134 tightly and adapted for repeated removal and application without losing its shape.

The tread pattern 304 defines a plurality of treads 316 spaced by a plurality of channels 314. The tread pattern 304 is preferably formed according to the anatomy of the condyle pad 300 to accommodate the knee during gait.

Figures 11D, 11E, 11F:
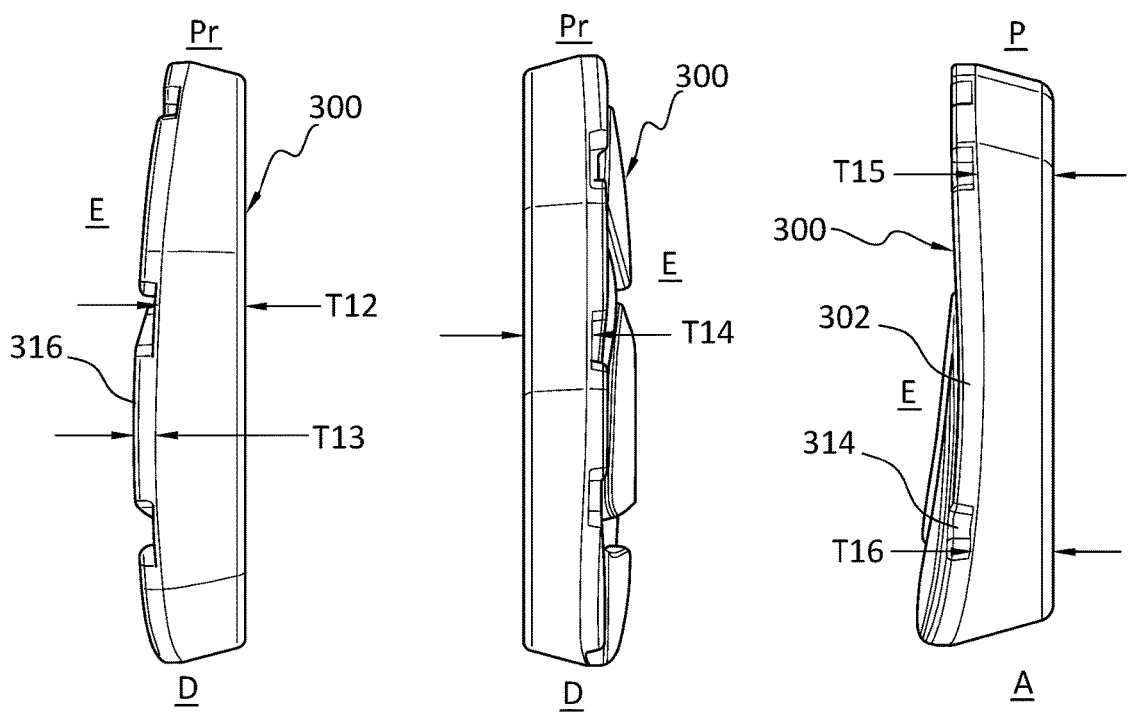
FIG. 11D is an elevational view of the condyle pad of FIG. 11A showing an anterior side.
FIG. 11E is an elevational view of the condyle pad of FIG. 11A showing a posterior side.
FIG. 11F is a top view of the condyle pad of FIG. 11A.

As shown in FIGS. 11D-11F, the body 302 has a compound curved shape. FIG. 11D shows the thickness as varying from proximal to distal ends with a greater thickness T12 toward the center of the body 302 along an anterior side of the condyle pad 300, whereby the plurality of treads 316 may generally extend uniformly from the body with a thickness T13. The posterior side of the body 302 may have a generally uniform thickness T14. From the top or proximal side of the body, the thickness T16 at the anterior side may progressively increase relative to the thickness T15 toward the posterior side. From these varying thickness, the condyle pad 300 can better fit the anatomy of a user's condyle, and offer a universal fit, as the EVA material may compress upon being between the rigid frame of the knee brace 200 and the user's condyle, accounting for the Q-angle and lateral shift of the first and second frame components 202, 204.

Figure 12A:
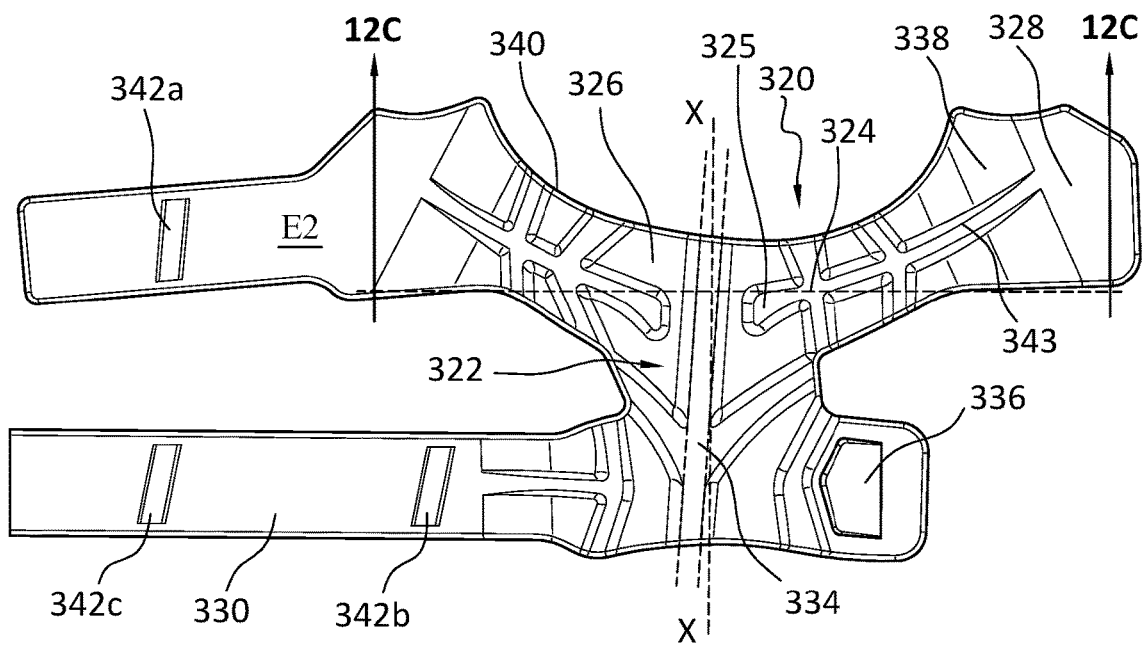
FIG. 12A is an elevational view of an exterior side of a liner for use in the orthopedic device of FIG. 9A.
Figure 12B:
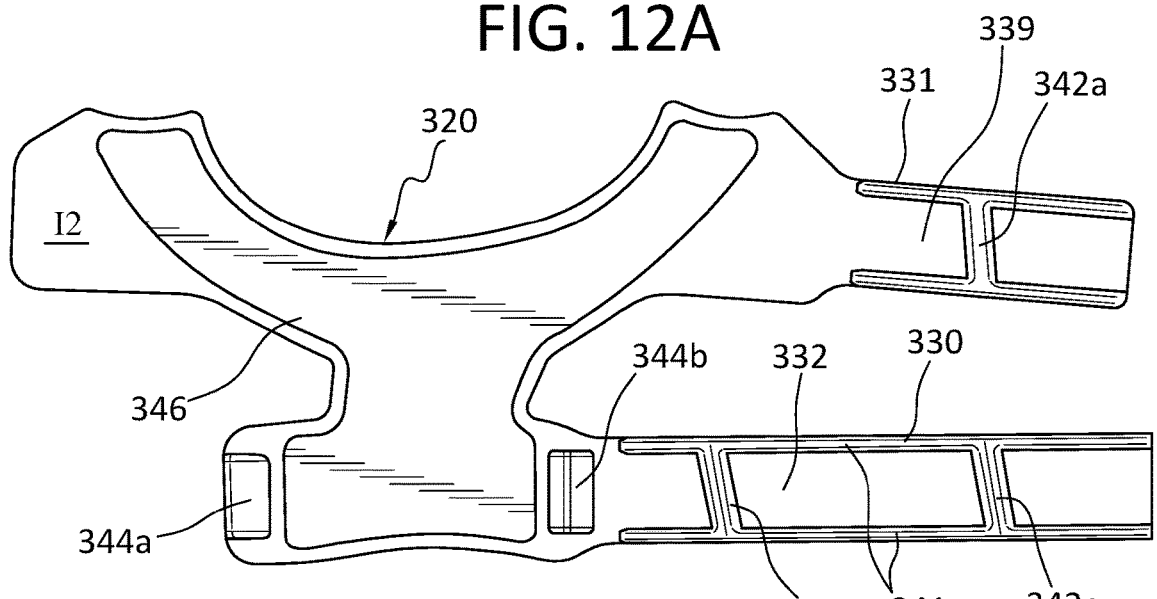
FIG. 12B is an elevational view of an interior side of the liner of FIG. 12A.
Figure 12C:
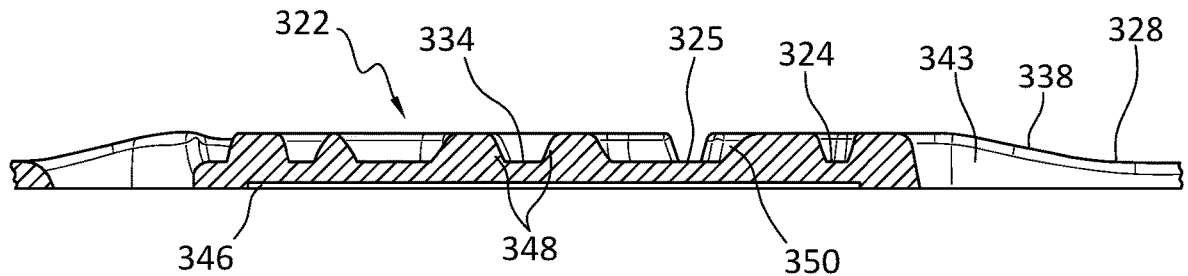
FIG. 12C is a cross-sectional view of the liner of FIG. 12A taken along line 12C-12C.

FIGS. 12A-12C exemplify a liner 320 contoured with a profile arranged for the second frame component 204; however, a liner may be likewise be provided with a profile arranged for the first frame component 202 and having similar properties. The liner 320 is preferably formed from EVA, as in the condyle pad 300. The liner 320 preferably forms a plurality treads 322 extending from an exterior side E2 and corresponding channels 324. The plurality of treads 322 and channels 324 are adapted to correspond to a user's leg with treads 322 adapted to grab and provide traction against the user's leg. As the liner 320 is adapted for the second frame component 204 and corresponding to the tibia, it may be formed thicker than a liner corresponding to the first frame component 202 to offer greater compression and bite, and to aid in impact attenuation.

For example, a center set of treads 326 is shaped to correspond to the anterior tibia, with a corresponding channel 334 extending along a length of the liner to minimize pressure on the anterior tibia. The channel 334 extends slightly obliquely relative to a vertical axis X-X of the orthopedic device, corresponding to the lateral shift and Q-angle. Within the treads 326, there are lateral recesses 325 adapted to the shape of the second frame component 204 to grasp the user's leg better. Flattened regions 328 are provided where minimal compression is required and treads 338 may transition in thickness to the flattened regions 328. As the liner 320 is preferably molded, indicia or messaging 336 may be molded into the liner for informational purposes.

FIG. 12C shows how the treads 322 have varying heights and profiles according to their location and how they match up to the anatomy of a leg. The treads 322 are arranged to naturally wrap to the profile of the second frame component 204 to avoid any wrinkling or the liner 320 fighting placement. For example, the treads 322 may define one or more channels or recesses 334, 324, 325 extending in substantially a similar direction, and divided by one or more individual treads forming walls 348, 350 between the channels 334, 324, 325.

The wall 350 may have a shallower profile than a profile of the wall 348; that is, the wall 350 may extend between a bottommost surface of the channel 325 and the topmost surface of an adjacent tread more gradually than the wall 348 extends between a bottommost surface of the channel 334 and the topmost surface of an adjacent tread. In embodiments, the channels 334, 324, 325 may extend the same distance or thickness into the liner 320.

The liner 320 may have a substantially flat backing layer 346 on an opposed or exterior side of the liner 320 from the treads 322. A profile 328 transitions the liner 320 from the treads 322 toward an outer edge portion 328, with a channel 343 generally extending perpendicularly from the treads 322 and the channels 334, 325. The profile 328 may extend between the topmost surface of the treads 322 and the topmost surface of the 328 more gradually than the wall 348 and the wall 350, but is not limited to such an arrangement and may take any suitable form or configuration.

FIG. 12B shows an interior side 12 of the liner 320. The interior side 12 defines a recessed section 346 contoured for the second frame component to fit therewith snugly. Portions outside the recessed section 346 extend outwardly therefrom and frame about the second frame component. The liner 320 forms strap sections 330, 331, whereby the strap sections 330, 331 enable a strap to be generally retained within the liner 320 to distribute better circumferential pressure exerted on a leg. Likewise, due to frictional characteristics of the EVA, at least enhanced as compared to a textile-based strap, the strap sections 330, 331 serve as an interface between the strap and user's leg.

The strap sections 330, 331 define strap loops 342a, 342b, 342c to retain the strap against the liner, and through which the strap sections 330, 331 extend. The strap sections 330, 331 form borders 341 and a recessed portion 332 located therebetween to yet further retain the straps against the liner. The liner 320 forms additional recesses 344a, 344b adapted at the corresponding medial and lateral arms of the second frame component 204.

Figure 13A:
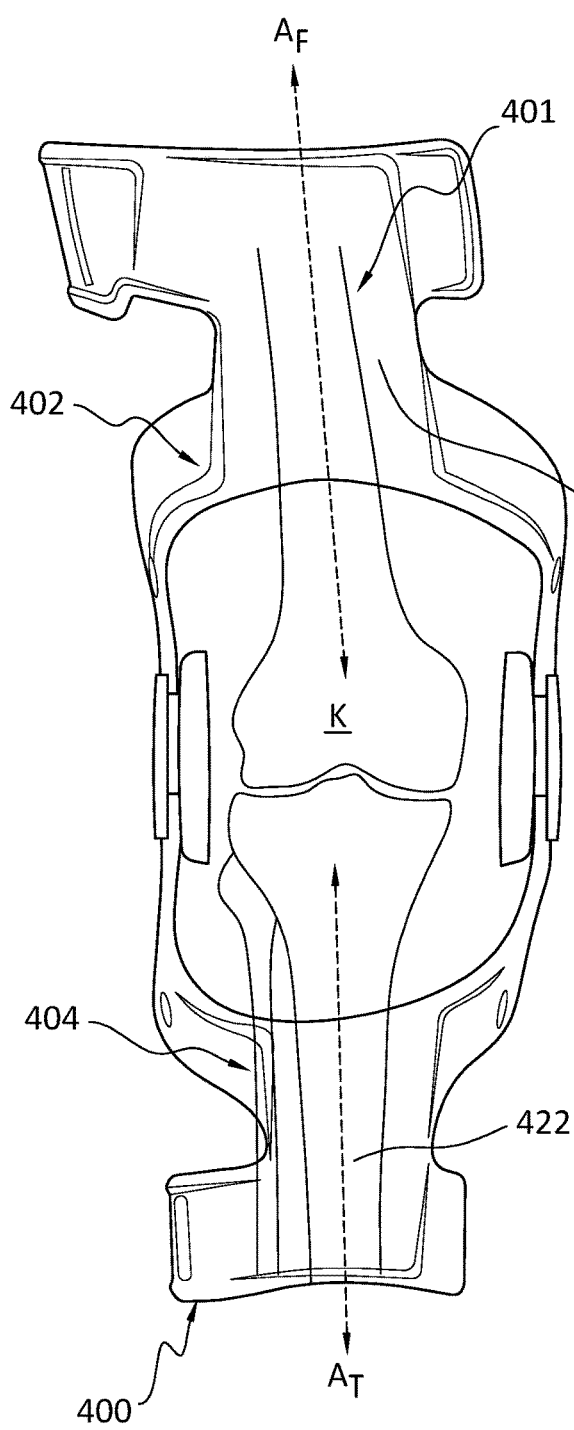
FIG. 13A is an elevational view of an orthopedic device worn according to the embodiments and worn on a leg.
Figure 13B:
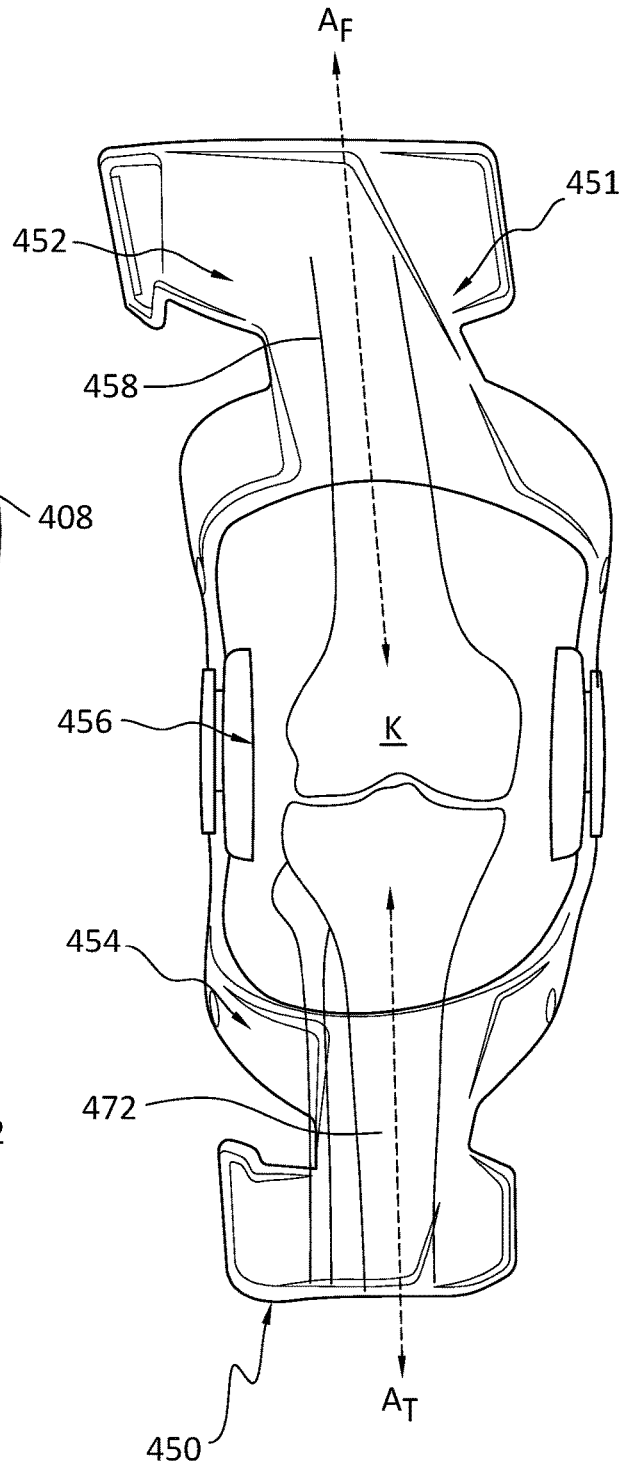
FIG. 13B is an elevational view of an orthopedic device according to FIG. 13A worn on a leg.

An orthopedic device according to the disclosed embodiments is shown in FIGS. 13A, 13B. An orthopedic device 400 is shown on a leg 401 of a user via an x-ray image. The orthopedic device 400 may comprise upper or first and lower or second frame components 402, 404 joined by a hinge assembly 406 as described in the embodiments of the disclosure. As described in the foregoing embodiments, the first and second frame components 402, 404 may define rigid masts 408, 422, respectively. The orthopedic device 400 is shown mounted on a leg 401, which may define an axis corresponding to the femur AF and an axis corresponding to the tibia AT. The rigid masts 408, 422 may correspond as described in the embodiments disclosed to the axes AF, AT, which, as shown are offset relative to each other relative to a knee K.

Likewise, an orthopedic device 450 is shown in FIG. 13B on a leg 451 of a user via x-ray image. The orthopedic device 450 comprises first and second frame components 452, 454 joined by a hinge assembly 456 according to the present disclosure. The first and second components 452, 454 may define rigid masts 458, 472 as described above. The rigid masts 458, 472 may advantageously follow and/or correspond to offset axes defined according to the femur AF and the tibia AT.

As seen in FIGS. 13A, 13B, the configuration of the orthopedic devices 400, 450 according to embodiments of the disclosure advantageously follow the natural contours and naturally offset axes of a human leg above and below a knee, improving the contact between the components of the orthopedic devices 400, 450 and the leg 401, 451 across the orthopedic devices 400, 450, minimizing uncomfortable pressure points, and enabling an off-the-shelf orthopedic device better configured to correspond to and comfortably fit and support a user's dimensions.

By providing an orthopedic device comprising a hinge assembly according to the embodiments, and having one or more of the above-described condyle pad, liner, and frame components according to the embodiments, the problem of orthopedic devices being poorly adapted to fit a variety of users in off-the-shelf applications and of putting undue pressure on portions of the anatomy are addressed. The orthopedic device embodiments advantageously provide for improved adaptation of an orthopedic device to better fit against, provide comfort for, and support a patient or user in rehabilitation, osteoarthritic complications, or other conditions.

Not necessarily all such objects or advantages may be achieved under any embodiment of the disclosure. Those skilled in the art will recognize that the disclosure may be embodied or carried out to achieve or optimize one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct a hinge assembly under principles of the present disclosure. Therefore, the embodiments described may be adapted to hinge assemblies for any suitable device, including orthopedic, prosthetic, medical, and other devices.

Although the hinge assembly has been disclosed in certain preferred embodiments and examples, it therefore will be understood by those skilled in the art that the present disclosure extends beyond the disclosed embodiments to other alternative embodiments or uses of the hinge assembly and apparent modifications and equivalents. It is intended that the scope of the present hinge assembly disclosed should not be limited by the disclosed embodiments described above but should be determined only by a fair reading of the claims that follow.

The invention claimed is:

1. A hinge assembly configured relative to a coronal plane of a human leg, comprising:
    a first hinge arm having a first longitudinal axis parallel with a lengthwise direction of the first hinge arm, the first hinge arm defining a first end portion having a first opening arranged along the first longitudinal axis and defining a first axis extending through the first opening, the first hinge arm being pivotable about the first axis, the first longitudinal axis being parallel to the coronal plane;
    a second hinge arm having a second longitudinal axis parallel with a lengthwise direction of the second hinge arm, the second hinge arm defining a second end portion having a second opening defining a second axis extending through the second opening and the second hinge arm being pivotable about the second axis;
    wherein when the first hinge arm and the second hinge arm are in an extension configuration, the first and second longitudinal axes are coaxial;
    wherein when the first and second longitudinal axes are coaxial, the second opening is arranged along a third longitudinal axis aligned along the second axis and running parallel to the first and second longitudinal axes;
    wherein when the first and second longitudinal axes are coaxial, the second opening is offset by a lateral distance perpendicular to the first and second longitudinal axes and measured between the first and second longitudinal axes and the third longitudinal axis;

wherein when the first and second longitudinal axes are coaxial, the first longitudinal axis of the first hinge arm is aligned with the second longitudinal axis of the second hinge arm;

wherein the first end portion and the second end portion define first and second geared profiles, respectively, arranged to cooperate with one another and form an interface;

wherein the first end portion bounded by the first geared profile portion has a first radius and is smaller than a second radius of the second end portion bounded by the second geared profile;

wherein the first radius is uniform along the first geared profile and the second radius is uniform along the second geared profile; and wherein the second opening is located posteriorly relative to and behind the coronal plane and the first and second longitudinal axes;

wherein the first hinge arm is located above or proximally relative to the second hinge arm.

2. The hinge assembly of claim 1, wherein the first and second radii are uniform along a limited periphery about the first and second end portions.

3. The hinge assembly of claim 1, wherein the first and second geared profiles of each the first end portion and the second end portion, respectively, form an identical number of teeth.

4. The hinge assembly of claim 3, wherein the teeth of the first and second end portions are similarly sized.

5. The hinge assembly of claim 1, wherein the second axis is perpendicularly and laterally offset from the second longitudinal axis.

6. The hinge assembly of claim 1, wherein the first end portion and the second end portion are connected to one another by a hinge plate, wherein the hinge plate is configured to retain the first and second end portions as connected, aside from the geared profiles.

7. The hinge assembly of claim 1, wherein the first end portion and second end portion only cooperate along the first and second gear profiles.

8. The hinge assembly of claim 1, wherein the first axis is centrally located on the first end portion.

* * * * *